United States Patent
Osumi

(10) Patent No.: US 9,823,130 B2
(45) Date of Patent: Nov. 21, 2017

(54) MULTI-ANGLE SPECTRAL IMAGING MEASUREMENT METHOD AND APPARATUS

(71) Applicant: OFFICE COLOR SCIENCE CO., LTD., Kumamoto-shi, Kumamoto (JP)

(72) Inventor: Masayuki Osumi, Kumamoto (JP)

(73) Assignee: OFFICE COLOR SCIENCE CO., LTD., Kumamoto-shi (JP)

( * ) Notice: Subject to any disclaimer, the term of this patent is extended or adjusted under 35 U.S.C. 154(b) by 0 days.

(21) Appl. No.: 15/265,816

(22) Filed: Sep. 14, 2016

(65) Prior Publication Data

US 2017/0010158 A1    Jan. 12, 2017

Related U.S. Application Data

(62) Division of application No. 14/395,476, filed as application No. PCT/JP2013/061671 on Apr. 19, 2013, now abandoned.

(30) Foreign Application Priority Data

Apr. 20, 2012  (JP) .................................. 2012-097170
Jun. 1, 2012   (JP) .................................. 2012-126389

(51) Int. Cl.
*G01J 3/28*        (2006.01)
*G01N 21/25*       (2006.01)
(Continued)

(52) U.S. Cl.
CPC .......... *G01J 3/2823* (2013.01); *G01J 3/0208* (2013.01); *G01J 3/0264* (2013.01); *G01J 3/0297* (2013.01);
(Continued)

(58) Field of Classification Search
CPC ........ G01J 3/28; G01J 3/02; G01J 3/42; G01J 3/52; G01J 3/46; G01J 3/12; G01N 21/25; G01N 21/27; G01N 21/57
See application file for complete search history.

(56) References Cited

U.S. PATENT DOCUMENTS 5,116,123 A  *  5/1992  Kuderer ................. G01J 3/2803
                                                   356/326
5,502,799 A  *  3/1996  Tsuji .......................... G01J 3/28
                                                   345/600
(Continued)

FOREIGN PATENT DOCUMENTS

CN          1732377 A      2/2006
CN        102066910 A      5/2011
(Continued)

OTHER PUBLICATIONS

Chinese Office Action for Application No. 2013800209788 dated Feb. 14, 2016.
(Continued)

*Primary Examiner* — Abdullahi Nur
(74) *Attorney, Agent, or Firm* — Orion Consulting, Ltd.; Joseph P. Farrar, Esq.

(57) ABSTRACT

A lighting device that emits illumination light from two or more angular directions onto a sample surface to be measured, an imaging optical lens, and a monochrome two-dimensional image sensor are provided. This configuration provides a method and an apparatus that take a two-dimensional image of the sample surface to be measured at each measurement wavelength and accurately measure multi-angle and spectral information on each of all pixels in the two-dimensional image in a short time. In particular, a multi-angle spectral imaging measurement method and apparatus that have improved accuracy and usefulness are provided.

7 Claims, 21 Drawing Sheets

(51) Int. Cl.
*G01J 3/50* (2006.01)
*G01J 3/12* (2006.01)
*G01J 3/46* (2006.01)
*G01J 3/02* (2006.01)
*G01N 21/57* (2006.01)
*G01N 21/84* (2006.01)
*G01N 21/27* (2006.01)
*G01J 3/42* (2006.01)
*G01J 3/52* (2006.01)

(52) U.S. Cl.
CPC ............. *G01J 3/12* (2013.01); *G01J 3/1256* (2013.01); *G01J 3/42* (2013.01); *G01J 3/46* (2013.01); *G01J 3/463* (2013.01); *G01J 3/501* (2013.01); *G01J 3/502* (2013.01); *G01J 3/504* (2013.01); *G01J 3/524* (2013.01); *G01N 21/255* (2013.01); *G01N 21/276* (2013.01); *G01N 21/57* (2013.01); *G01N 21/8422* (2013.01); *G01J 2003/1226* (2013.01); *G01J 2003/2826* (2013.01); *G01N 2201/061* (2013.01)

(56) References Cited

U.S. PATENT DOCUMENTS

| 2003/0169421 A1 | 9/2003 | Ehbets |
| 2006/0197083 A1 | 9/2006 | Suzuki et al. |

FOREIGN PATENT DOCUMENTS

| CN | 102361580 A | 2/2012 |
| EP | 0399057 A1 | 11/1990 |
| EP | 0570003 A2 | 11/1993 |
| EP | 1577652 A1 | 9/2005 |
| JP | S54-023587 A | 2/1979 |
| JP | S60-41731 A | 3/1985 |
| JP | H07-270238 A | 10/1995 |
| JP | 2001-099711 A | 4/2001 |
| JP | 2001-264174 A | 9/2001 |
| JP | 2003-337067 A | 11/2003 |
| JP | 2004-226262 A | 8/2004 |
| JP | 3933581 B | 9/2004 |
| JP | 2005-114529 A | 4/2005 |
| JP | 2005-181038 A | 7/2005 |
| JP | 2005-195365 A | 7/2005 |
| JP | 2006-153498 A | 6/2006 |
| JP | 2007-333726 A | 12/2007 |
| WO | WO-02/082063 A1 | 10/2002 |

OTHER PUBLICATIONS

Masayuki Osumi, "The Evaluation Method of Effect Material applied Gonio-photometric Spectal Imaging", Journal of the Color Science Association of Japan, May 1, 2012, vol. 36, No. Supplement, pp. 88-89.

Kazutaka Tonsho et al: 11Development of Gonia-photometric Imaging System for Recording Reflectance Spectra of 3D Objects, SPIEE 4663, Jan. 19, 2002 (Jan. 19, 2002). XP055230520, Retrieved from the Internet: URL: http:f/133.82.248.84/-tsumura/Tsumura/papers/EI2002_0765691.pdf [retrieved on—Nov. 23, 2015].

Extended European Search Report for Application No. EP13779080 dated Dec. 1, 2015.

* cited by examiner

L* SCALE:   0.0 to 200.0
a* SCALE: -100.0 to 100.0
b* SCALE: -100.0 to 100.0

MULTI-ANGLE SPECTRAL IMAGING MEASUREMENT METHOD AND APPARATUS

CROSS-REFERENCE TO RELATED APPLICATIONS

This application is a divisional application under 35 U.S.C. §121 of prior U.S. Application No. 14/395,476 filed on Oct. 18, 2014, which is a National Stage entry under 35 U.S.C 371(c) of International Application No. PCT/JP2013/061671, filed on Apr. 19, 2013, which in turn claims priority to Japanese Application Nos. 2012-097170, filed on Apr. 20, 2012, and 2012-126389, filed on Jun. 1, 2012, the entire disclosures of which are hereby incorporated by reference herein.

TECHNICAL FIELD

The present invention relates to any fields, such as paint, coating, textile, printing, and plastic, in which colors of surfaces of objects are measured and to a multi-angle spectral imaging measurement method and apparatus used in measurement and evaluation, and manufacturing based on the measurement and evaluation.

BACKGROUND ART

Design aesthetic is one of the very important added-values of industrial products today. Accordingly, there are many products that have various kinds of texture and surface structures. For example, the outer coating materials of automobiles contain various kinds of effect materials and accordingly their surfaces have extremely minute glitter reflective and granular texture. Furthermore, colors significantly change according to variations in combinations of effect materials, pigments and other materials, layer structures of coating, and geometrical conditions of lighting and observation directions. In particular, the advent of interference effect materials in recent years has added variety to colors and texture. In addition to outer coating of automobiles, the surface structures of other products such as interior materials, furniture, buildings, electric appliances, electronic devices, cosmetics, and packages have become complex regardless of inclusion of effect materials. Like outer coating of automobiles, the colors and texture of products change in various ways depending on texture and optical geometrical conditions. Furthermore, wood products and textile products as well as coated products exhibit color changes and texture changes depending on optical geometrical conditions. Not only industrial products, but also skin and biological matters exhibit color changes and texture changes depending on optical geometrical conditions.

Product development of designs and materials, manufacturing and quality control, and marketing such as advertisements have required a high level of visual evaluation by experienced people and therefore have required time and human resource consuming and required huge energy and enormous efforts. There are demands for establishment of methods for accurately measuring and evaluating colors of surfaces of products and means for accurately representing images such as CGs.

Thus, it is desired to establish physical means and an evaluation method for accurately and stably measuring image color information at multiple angles with simple operations. Note that as color measurement, spectral measurement is essential especially for colors of objects containing interference effect materials because of its accuracy and capability of measuring a wide range of colors.

Patent document 1 discloses a technique that uses light dispersed by a prism or a diffraction grating to acquire spectral information that differs among parts of an image.

Patent document 2 discloses a technique relating to a multi-angle spectral imaging apparatus including a rotary illumination light source and a multispectral camera.

Patent document 3 discloses a technique in which a white reference surface is provided around an entire sample surface in order to correct time fluctuations in an illumination light source.

Patent document 4 discloses a technique that uses a lighting device including a plurality of monochromatic LEDs that are arranged in a row and capable of emitting light rays of different colors to illuminate a sample surface and take an image when multi-angle spectral measurement is performed.

Patent document 5 discloses a technique relating to a spectral measurement system including a spectrometer that measures a first spectrum of a subject under ultraviolet illumination light and a second spectrum of the subject under visible illumination light.

Patent document 6 discloses a technique relating to a color measurement apparatus that measures spectral characteristics of a sample and performs computations.

CITATION LIST

Patent Literature

Patent document 1: Japanese Patent No. 3933581
Patent document 2: Japanese Patent Laid-Open No. 2005-181038
Patent document 3: Japanese Examined Patent Publication No. 60-041731
Patent document 4: Japanese Patent Laid-Open No. 2004-226262
Patent document 5: Japanese Patent Laid-Open No. 2003-337067
Patent document 6: Japanese Patent Laid-Open No. 2007-333726

SUMMARY OF INVENTION

Technical Problems

The technique disclosed in Patent document 1 provides a method for acquiring spectral information that differs among parts of an image. However, the spectral information differs only among pixels and spectral information with different wavelengths or the like for different pixels cannot be acquired at all of the pixels. Furthermore, means for correcting changes in the amount of light and changes in exposure time during measurement is not configured. Accordingly, it is difficult for the technique to provide high-precision measurement that is practical in manufacturing coating materials or product manufacturing that involves coating. Moreover, since the lighting device illuminates from only one angular position that is greater than 40 degrees, the field angle of a recording device needs to be wide, causing distortion near the rim of an imaging lens which is generally used in the recording device.

The technique disclosed in Patent document 2 relates to a multi-angle spectral imaging apparatus including an illumination light source and a multispectral camera. However, the illumination light source disclosed is a light source that rotates illumination from one position or one illuminant, or a configuration in which a sample is rotated. This makes accurate measurement difficult and requires a mechanism for causing rotation, which adds to complexity to the mechanism of the imaging apparatus.

The technique disclosed in Patent document 3 applies light from a light source to light reflected from an object to be measured and to background light, receives light rays are received at a light receiver, then compares both light rays with each other but does not acquire spectral information by taking an image of applied light.

The technique disclosed in Patent document 4 uses two fixed lighting devices for measurement. A problem with the technique is that since each of the lighting devices has monochrome LEDs that are arranged in a row and emit light rays of different colors and the LEDs are turned on and off independently of each other, the different light-emitting LEDs emit light to an object to be measured at different angles and information acquired with an image pickup device differs accordingly.

The technique disclosed in Patent document 5 provides a plurality of light emitting parts that have a plurality of different spectral energy distributions. However the technique has a problem that since the light emitting parts are provided separately, the different light emitting parts emit light to an object to be measured at different angles and information acquired with a spectrometer differs accordingly.

The technique disclosed in Patent document 6 only performs image computations based on information acquired with a spectrometer.

In order to acquire features of and evaluation information about effect materials containing complex structural coloration, image measurement that is capable of multi-angle measurement in which optical geometrical conditions based on lighting and observation directions can be changed in a wide color gamut is required and effective. Furthermore, image analysis calculations for quantifying features of measured spectral imaging information are required.

However, such an apparatus has not been in practical use and existing methods provide extremely small amount of information or require enormous time for data measurement. In addition, effective means for image analysis calculation combined with such an apparatus is needed. On the other hand, special interference effect materials are being often used in modern coating of automobiles. The interference effect materials contain extremely fine and high-brightness glittering reflected colors that has a wide color representation range. In order to effectively use multi-angle information and perform accurate image analysis calculations for evaluating features of such coating colors, highly precise and precise measurement needs to be performed with a high dynamic range and in a wide color gamut over a whole image.

In light of the problems with the existing techniques described in the Background Art section, an object of the present invention is to provide a method and an apparatus that efficiently measure information such as multi-angle spectral information on each pixel of a surface of an object in a short time and, more specifically, to implement a more accurate and practical multi-angle spectral imaging measurement method and apparatus.

Another object is to implement a multi-angle spectral imaging measurement method for correcting changes in optical geometrical conditions for sample surfaces having a three-dimensional geometry and an apparatus therefor.

Solution to Problems

In order to acquire features of and evaluation information about effect materials containing complex structural coloration, image measurement that is capable of multi-angle measurement in which optical geometrical conditions based on lighting and observation directions can be changed in a wide color gamut is required and effective.

In order to solve the problems, according to the present invention, a two-dimensional image sensor capable of taking an image in a direction perpendicular to a sample surface is provided, lighting devices are placed at certain angles with respect to the direction perpendicular to the sample surface, and changes in optical geometrical conditions from pixel to pixel in the X axis and Y axis directions in an image are used while applying illumination light from two or more angular directions, thereby measuring multi-angle spectral imaging information.

The spectral measurement uses a white light illumination/spectral light receiving method with a band-pass filter having a passband for each constant wavelength, a liquid-crystal tunable filter that allows passband tuning, an acoustooptic element or the like at a position between the two-dimensional image sensor and the sample surface. Alternatively, a spectral illumination method with a spectral light source device capable of emitting monochromatic light with each measurement wavelength as illumination light is used. Alternatively, a combination of a spectral light receiving method and a spectral illumination method is used so that fluorescent color can be measured.

Spectral data measured on each pixel is converted to color numeric values such as tristimulus values of CIE, CIELAB values, RGB values, or Munsell color system values, then the color numeric values are provided to numeric value calculation means that uses numeric values for a three-dimensional structure of distributions in a LAB space based on optical geometrical conditions, space frequency analysis, information entropy or the like to compare and evaluate features of a surface of an object.

Three-dimensional geometry measurement means is incorporated in the multi-angle spectral imaging apparatus, whereby three-dimensional geometry information on the sample surface is used to obtain the direction normal to the sample surface, and differences in optical geometrical conditions and differences in irradiation energy of light per unit area due to displacement and difference in inclination are corrected.

Advantageous Effects of Invention

According to the present invention, a method and an apparatus that efficiently measure information such as multi-angle spectral information on each pixel of a surface of an object in a short time can be provided and, more specifically, a more accurate and practical multi-angle spectral imaging measurement method and apparatus can be implemented. Furthermore, since the field angle range of the imaging lens can be reduced by using irradiation of illumination light from two or more angular directions, distortion near the rim of the imaging lens can be reduced to enable accurate and extensive spectral measurement of color information. Moreover, a high spatial resolution can be achieved in a short time by measuring various and continuous optical geometrical conditions at a time. Furthermore, since spectral information is obtained as an image, minute glittering reflection can be captured. In addition, flexible use of distribution information in a color space and data processing in combination with multi-angle information is possible, such as averaging an image partially or for each optical geometrical condition. Moreover, incorporation of the three-dimensional geometry measurement means enables measurement of three-dimensional geometry information on a sample surface, thereby allowing correction of differences in irradiation energy of light per unit area due to changes in optical geometrical conditions, displacement, and differences in inclination. By measuring skin or biological matters, the present invention can contribute to research and development in the medial and cosmetics fields.

DETAILED DESCRIPTION OF EMBODIMENTS

Embodiments of the present invention will be described below with reference to drawings.

(Measurement Mechanism)

Figure 1:
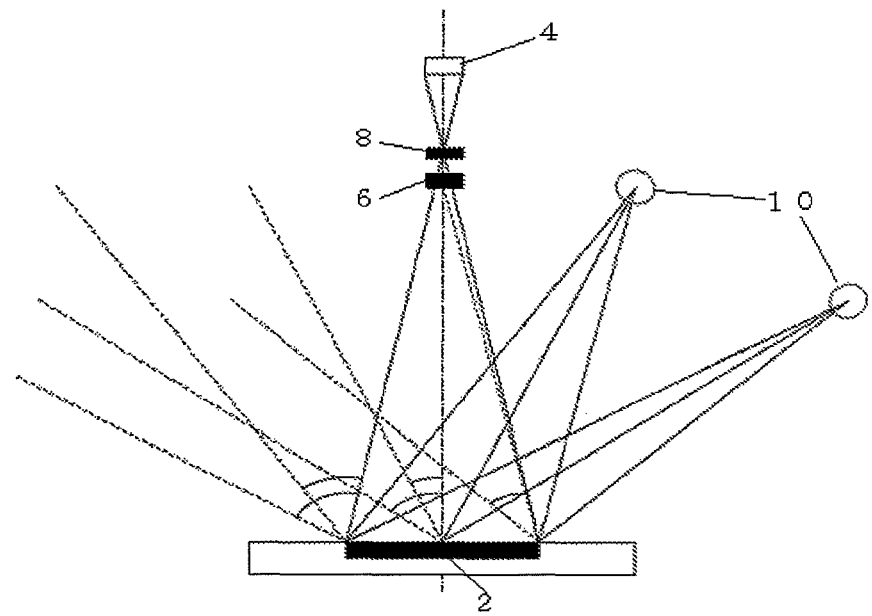
FIG. 1 is a diagram schematically illustrating a configuration of the present invention.

FIG. 1 is a diagram schematically illustrating a configuration of the present invention. An embodiment of a multi-angle spectral imaging apparatus of the present invention includes a monochrome two-dimensional image sensor 4 that is disposed in the direction perpendicular to a flat sample surface 2 to be measured and acquires a gray-scale image, an optical lens 8 that forms an image on the monochrome two-dimensional image sensor, spectroscopic means 6, such as a liquid-crystal tunable filter, that is disposed in a predetermined position between the sample surface 2 to be measured and the optical lens 8 and whose passband is tunable, and a lighting device 10 having energy required for measurement in a measurement waveband. One embodiment of the present invention is configured with a white reference surface 12 disposed around the sample surface 2 to be measured in parallel with the sample surface to be measured. An image of the white reference surface is taken together with the sample surface 2 to be measured. This image is used for correction made for accommodating changes in the amount of light of illumination and changes and errors in exposure time of an image pickup device during measurement.

(Optical Geometrical Conditions)

Figure 2:
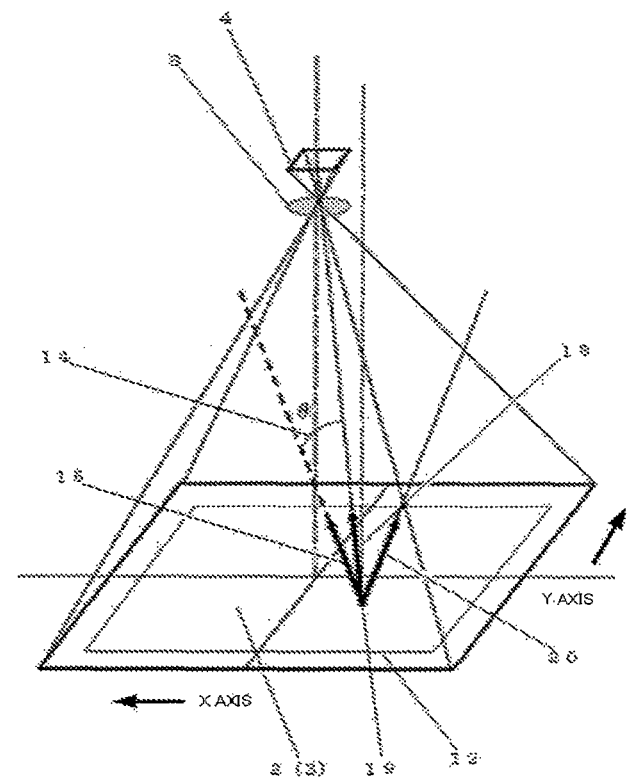
FIG. 2 is a diagram illustrating optical geometrical conditions in the present invention.

Optical geometrical conditions of images, illumination and light reception/observation will be described below. FIG. 2 is a diagram illustrating optical geometrical conditions in the present invention. Light emitted from the lighting device 10 illuminates the sample surface 2 to be measured and the white reference surface 12. The monochrome two-dimensional image sensor 4 and the optical lens 8 are disposed so that the sample surface 2 to be measured and the white reference surface 12 are included together in an image taken. Note that the spectroscopic means 6 is omitted from FIG. 2.

Light emitted from the lighting device 10 illuminates the sample surface 2 to be measured and the white reference surface 12. The illumination direction is dependent on the geometry being illuminated and varies from position to position on the sample surface 2 to be measured and the white reference surface 12 with respect to the direction perpendicular to the sample surface 2 to be measured and the white reference surface 12. Specular reflection direction is opposite to the illumination direction, namely the mirrored direction of the illumination direction. The direction in which the pixels of the monochrome two-dimensional image sensor 4 taking an image of the sample surface 2 to be measured and the white reference surface 12 receive light varies from pixel to pixel and the unit vector 18 is denoted by $P_{ij}$. Here, i,j represent position of a pixel in the X axis and the Y axis of the image, respectively. In other words, (i, j) represents the coordinates of each pixel on a two-dimensional image.

The unit vector 20 on the image in the illumination direction is denoted by $I_{ij}$ and the corresponding unit vector 16 in the specular reflection direction is denoted by $S_{ij}$. The angle of the unit vector 18 in the light receiving direction with respect to the specular reflection direction of illumination is generally called aspecular angle 14 (hereinafter referred to as the "aspecular angle"). Metallic colors and pearlescent colors used for outer coating of automobiles change in hue (lightness, chroma and hue) depending on this angle. The aspecular angle at each pixel on an image is denoted by $\delta_{ij}$ and can be written as Formula 1. Note that, for clarity, positions are described as positions on the sample surface 2 to be measured or on the white reference surface 12 that correspond to pixels (i, j) 19 of the monochrome two-dimensional image sensor 4 in FIG. 2.

$$\delta_{ij}=\cos^{-1}(p_{ij} \cdot S_{ij}) \quad \text{[Expression 1]}$$

Here, $p_{ij} \cdot S_{ij}$ represents the inner product of $P_{ij}$ and $S_{ij}$.

As can be seen from FIG. 2, the aspecular angle $\delta_{ij}$ in the pixels of the monochrome two-dimensional image sensor 4 differs for different i and j and therefore has different angle information.

Based on FIG. 2, a method for calculating the aspecular angle will be described in detail. Geometrical conditions for point P are: the zenith angle of illumination denoted by $\theta_{il}$, the azimuth angle of illumination measured counterclockwise with respect to the X axis, denoted by $\phi_{il}$, the zenith angle of light reception, denoted by $\theta_{rsv}$, and the azimuth angle of light reception measured counterclockwise with respect to the X axis denoted by $\phi_{rsv}$. Assuming that the geometrical conditions ($\theta_{ij}$, $\phi_{ij}$, $\theta_{rsv}$, $\phi_{rsv}$) have been obtained by calculations, which will be described later, and letting ($n_{xa}$, $n_{ya}$, $n_{za}$) denote a unit vector in the specular reflection direction corresponding to the illumination direction and ($n_{xr}$, $n_{yr}$, $n_{zr}$) denote a unit vector in the light reception direction, then the angles of specular reflection can be written as $$\theta_{as}=\theta_{il}$$

$$\phi_{as}=\phi_{il}+\pi \quad \text{[Expression 2]}$$

Therefore, $$n_{xa}=\sin(\theta_{as}) \cdot \cos(\phi_{as})$$

$$n_{ya}=\sin(\theta_{as}) \cdot \sin(\phi_{as})$$

$$n_{za}=\cos(\theta_{as}) \quad \text{[Expression 3]}$$

On the other hand, in the case of light reception angle $$n_{xr}=\sin(\theta_{rsv}) \cdot \cos(\phi_{rsv})$$

$$n_{yr}=\sin(\theta_{rsv}) \cdot \sin(\phi_{rsv})$$

$$n_{zr}=\cos(\theta_{rsv}) \quad \text{[Expression 4]}$$

The angle is inversely calculated from the inner product as $$\delta_{ij}=\cos^{-1}(n_{xa} \cdot n_{xr}+n_{ya} \cdot n_{yr}+n_{za} \cdot n_{zr}) \quad \text{[Expression 5]}$$

Here, $\delta_{ij}$ is a typical angle condition for identifying optical features of effect materials. It is useful that color space distributions are calculated and statistical parameters are calculated from an image in a region where $\delta_{ij}$ is the same.

Figure 3:
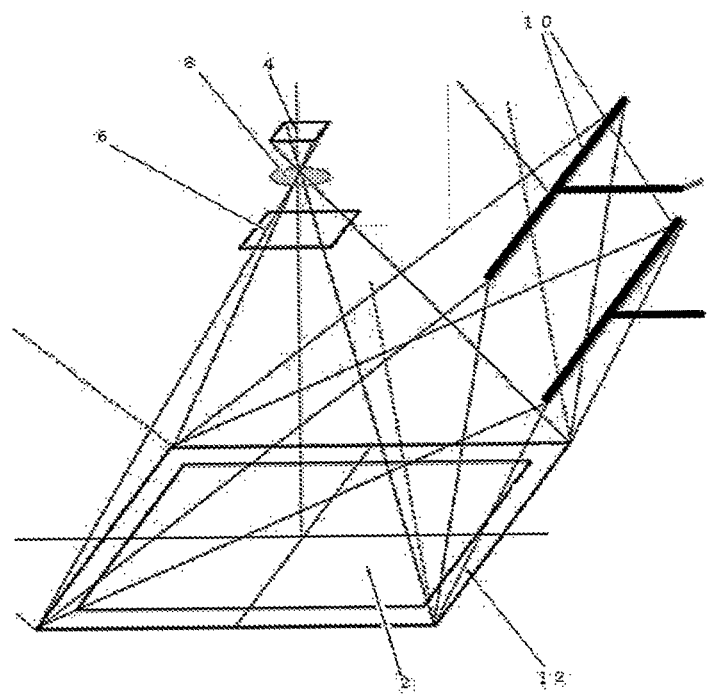
FIG. 3 is a diagram illustrating an embodiment that uses a linear lighting device.
Figure 4:
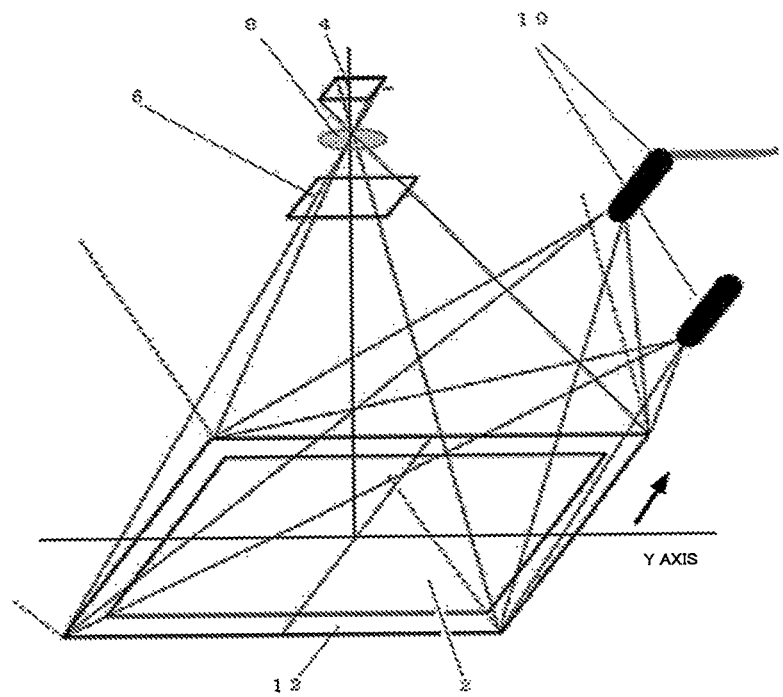
FIG. 4 is a diagram illustrating an embodiment that uses a spot lighting device.

The lighting device 10 used is linear (a linear light source) as illustrated in FIG. 3 or a spot (a point light source) as illustrated in FIG. 4. The optical lens 8 and the spectroscopic means 6 may be replaced with each other on condition that they can fulfil their respective functions. In the case of linear illumination, different angle information is available in the X axis or Y axis direction of the image, depending on the direction in which the lighting device 10 is placed. In the case of a spot illumination, the illumination angle and light reception angle vary in both X and Y axis directions of the image and therefore different angle information in both directions are available.

Figure 7:
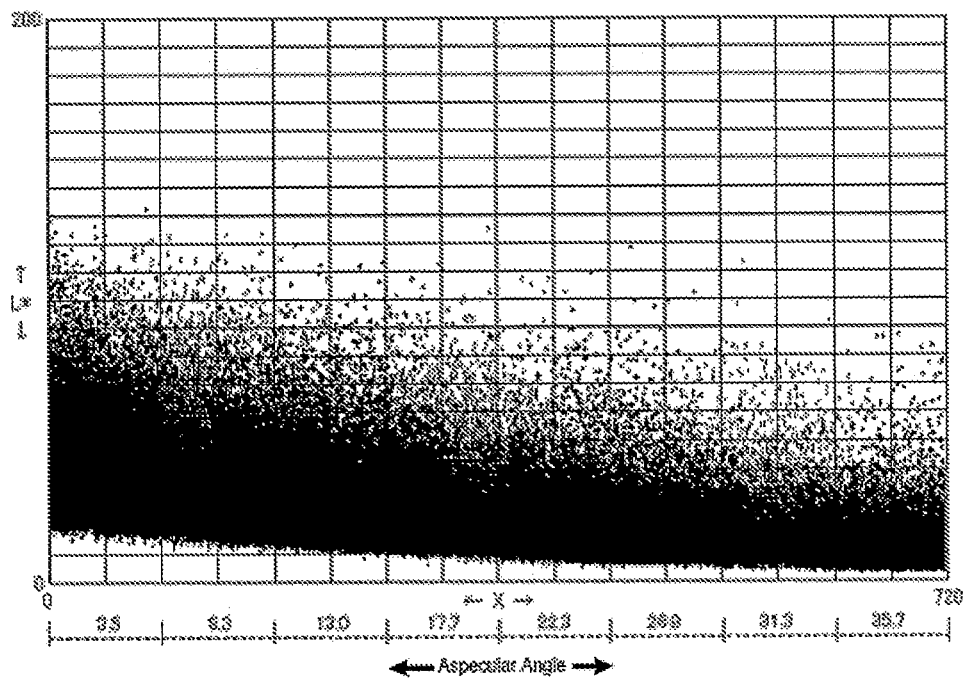
FIG. 7 is a graph illustrating distributions of L* when a lighting device is set at an angle of 20 degrees.
Figure 8:
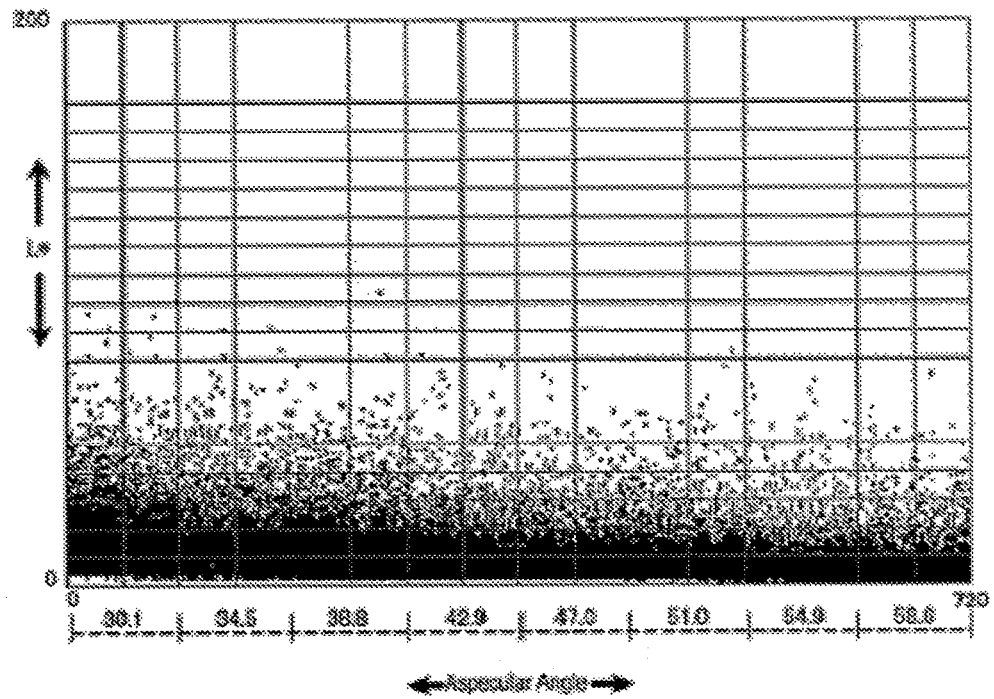
FIG. 8 is a graph illustrating distributions of L* when the lighting device is set at an angle of 45 degrees.

Here, since the sample surface 2 to be measured has a two-dimensional extent, the aspecular angle varies from position to position on the sample surface 2 to be measured and the white reference surface 12. FIG. 7 illustrates a distribution of L* obtained from an image measured when the lighting device is set at 20 degrees and FIG. 8 illustrates a distribution of L* obtained from an image measured when the lighting device is set at 45 degrees.

Means for acquiring spectral information by using light emitted from a point or liner illumination light source device and reflected by a sample surface and changes in optical geometrical conditions depending on positions on a sample surface will be described in further detail.

Figure 17:
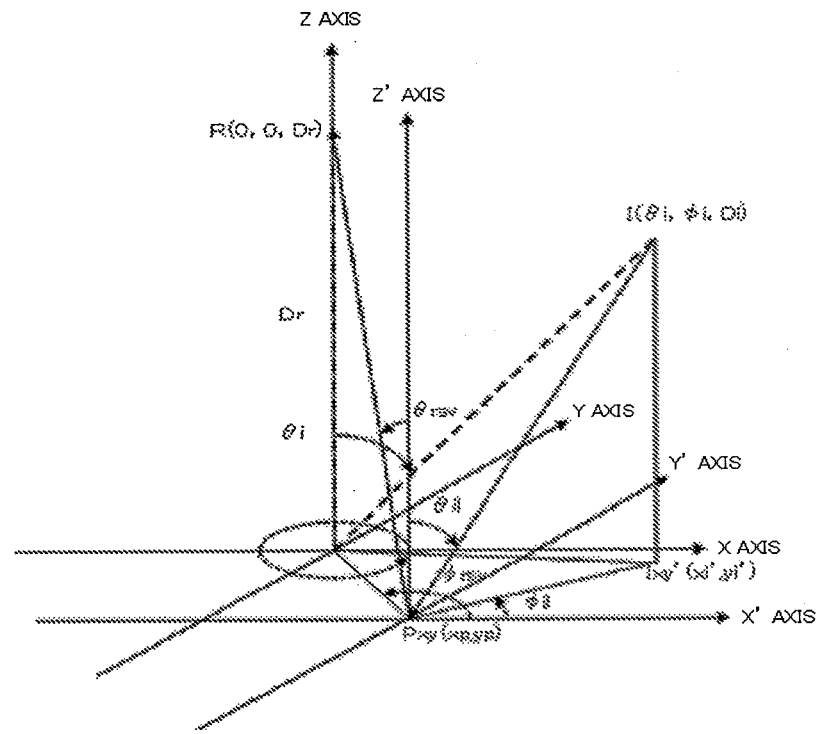
FIG. 17 is a diagram illustrating means for acquiring spectral information when a point light source is used.

FIG. 17 illustrates the case of the point light source. A position on the sample surface is denoted by $P_{XY}(x_p, y_p)$, the position of an illuminant is denoted by $I(\theta_i, \phi_i, D_i)$, and a light receiving position (focal point position) is denoted by $R(0, 0, D_r)$. Here, x and y are positions in the X axis direction and Y axis direction, respectively, on the sample surface, $\theta$ is a zenith angle, $\phi$ is an azimuth angle measured counterclockwise from the X axis, $D_i$ is the distance from the coordinate origin of the sample surface to the light source, and $D_r$ is the distance from the coordinate origin of the sample surface to an image pickup device. It is assumed that the image pickup device has a field angle large enough to cover an image taking range of the sample surface. Geometrical conditions of illumination and light receiving at position P can be represented by the zenith angle of the illumination, the azimuth angle of the illumination, the zenith angle of the light reception, and the azimuth angle of the light reception. Then the position of the illumination can be written as:

$$x_i = D_i \cdot \sin(\theta_i) \cdot \cos(\phi_i)$$

$$y_i = D_i \cdot \sin(\theta_i) \cdot \sin(\phi_i)$$

$$z_i = D_i \cdot \cos(\theta_i) \quad \text{[Expression 6]}$$

A relative coordinate position of the illumination on the xy plane for point P can be written as:

$$x_i' = x_i - x_p$$

$$Y_i' = y_i - y_p \quad \text{[Expression 7]}$$

and the relative coordinate position of light reception in the xy plane for point P can be written as: [Expression 8]

$$x_r' = -x_p$$

$$y_r' = -y_p$$

Then geometric conditions ($\theta_{il}$, $\phi_{il}$, $\theta_{rvs}$, $\phi_{rvs}$) are $$\theta_{il} = \pi/2 - \tan^{-1}(Z_i/\sqrt{(x_i')^2 + (y_i')^2}) \text{ (sqrt represents square root; the same applies to the following formulas.)}$$

$$\phi_{il} = \tan^{-1}(y_i'/x_i')$$

$$\theta_{rsv} = \pi/2 - \tan^{-1}(z_r'/\sqrt{(x_r')^2 + (y_r')^2})$$

$$\phi_{rsv} = \tan^{-1}(y_r'/x_r') \quad \text{[Expression 9]}$$

Figure 18:
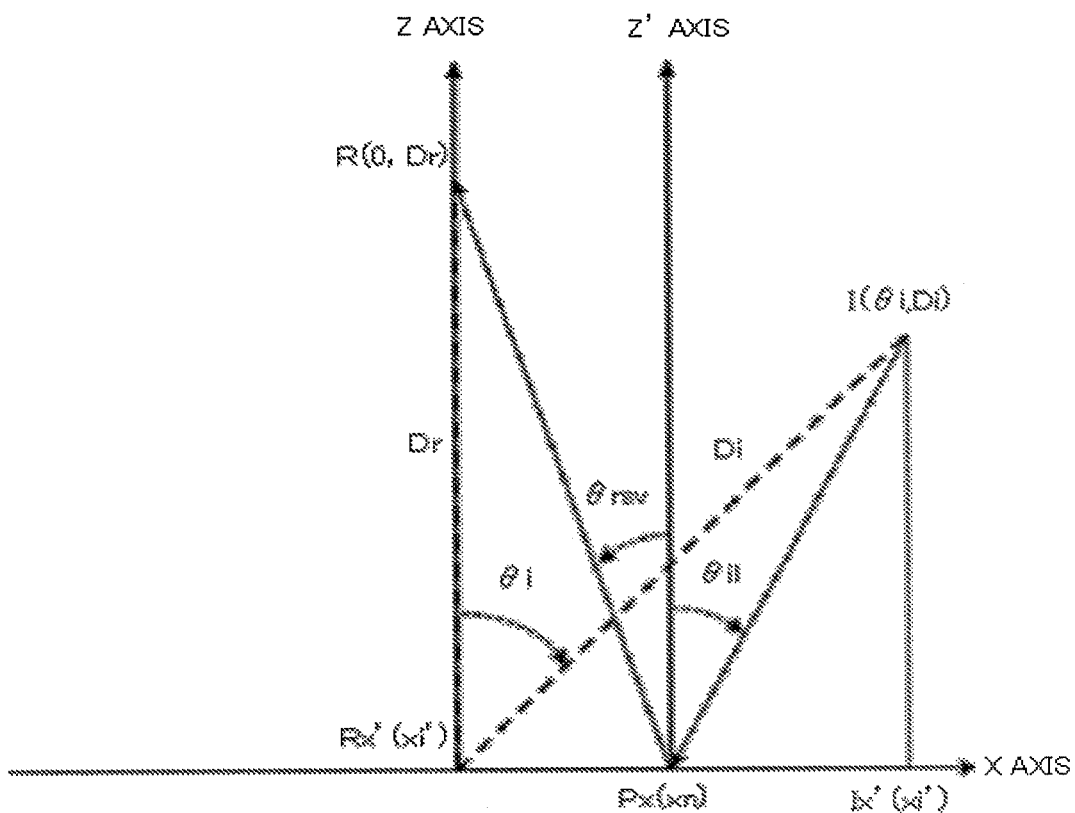
FIG. 18 is a diagram illustrating means for acquiring spectral information when a linear light source is used.

FIG. 18 illustrates the case of a linear light source. If the light source is disposed parallel to the Y axis direction, illumination is uniform along the Y axis and optical geometrical conditions in this case are: a position on the sample surface denoted by $P(x_p)$, the illumination position denoted by $I(\theta_i, D_i)$, and the light receiving position (focal point position) denoted by $R(0, D_r)$. Here, x is a position in the X axis direction and the Y axis direction on the sample surface, $\theta$ is a zenith angle, $D_i$ is the distance from the coordinate origin to the illumination and $D_r$ is the distance from the coordinate origin to an image pickup device. It is assumed that the image pickup device has a field angle large enough to cover an image taking range of the sample surface. Geometrical conditions of illumination and light receiving at position P can be represented by the zenith angle of the illumination, the azimuth angle of the illumination, the zenith angle of the light reception, and the azimuth angle of the light reception. Then the position of the illumination can be written as:

$$x_i = D_i \cdot \sin(\theta_i)$$

$$z_i = d_i \cdot \cos(\theta_i) \quad \text{[Expression 10]}$$

A relative coordinate position of the illumination on the xy plane for point P can be written as:

$$x_i' = x_i - x_p$$

$$z_i' = z_i \quad \text{[Expression 11]}$$

and the relative coordinate position of light reception in the xy plane for point P can be written as:

$$x_r' = -x_p$$

$$z_r' = -D_r \quad \text{[Expression 12]}$$

Then geometric conditions ($\theta_{il}$, $\theta_{rsv}$) are $$\theta_{il} = \pi/2 - \tan^{-1}(z_i'/|x_i'|)$$

$$\theta_{rsv} = \pi/2 - \tan^{-1}(z_r'/|x_r'|) \quad \text{[Expression 13]}$$

Figure 19:
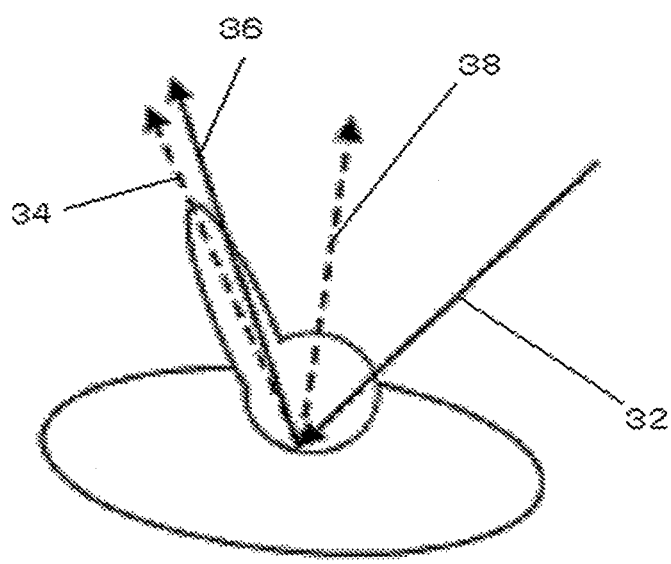
FIG. 19 is a diagram illustrating measured value changes with changes in geometrical conditions due to the orientation of effect materials.

FIG. 19 illustrates changes of measured values with changes in geometrical conditions due to the orientation of effect materials. The effect materials have glittering reflection properties including specular reflection on its surface and exhibits strong directionality of reflection in the specular reflection direction. Because of the extremely strong reflection in the specular reflection direction, the amount of reflected light rapidly decreases as the distance of the observation position from the specular reflection direction increases. While glitter additive sizes are typically in the range of several micrometers to several tens of micrometers, some effect materials exceed 100 μm in size. This occurs because there are fluctuations in the distribution of light in the coating film formed by splay coating.

Slight changes in optical geometrical conditions at each wavelength can lead to significant changes in the amount of reflected light near the specular reflection, which can prevent spectroscopic means from accurately measuring glittering reflection and can lead to a significant difference in distributions in the color space. For instance, effect materials made of aluminum flakes are silver in color and actually have a substantially constant reflectance factor at each wavelength, but if optical geometrical conditions vary from wavelength to wavelength, the spectral reflectance factor vary from wavelength to wavelength, which will produce false colors. In the case of interference effect materials, changes in optical geometrical conditions will change interference conditions and will significantly affect the spectral reflectance factor and color values.

Figure 20:
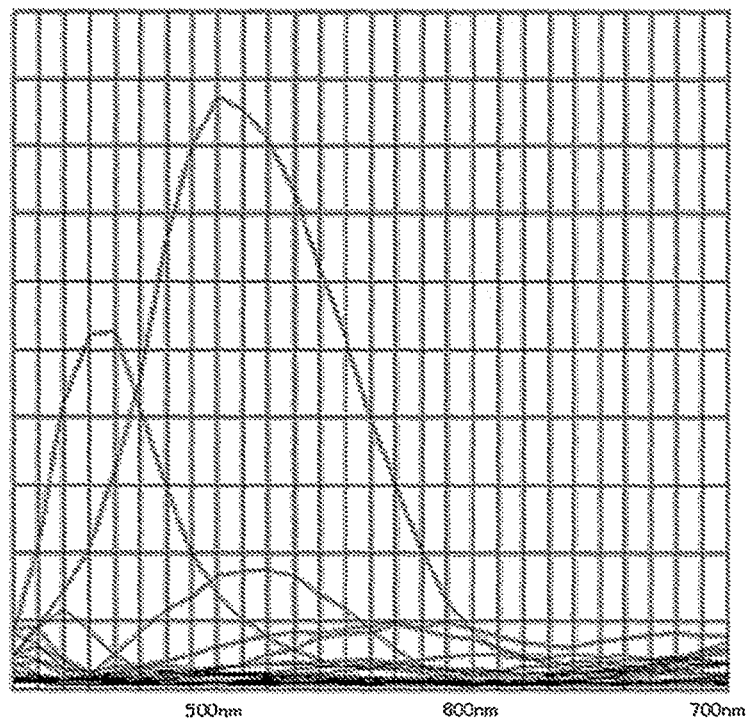
FIG. 20 is a diagram illustrating example measurements of interference effect materials.
Figure 21:
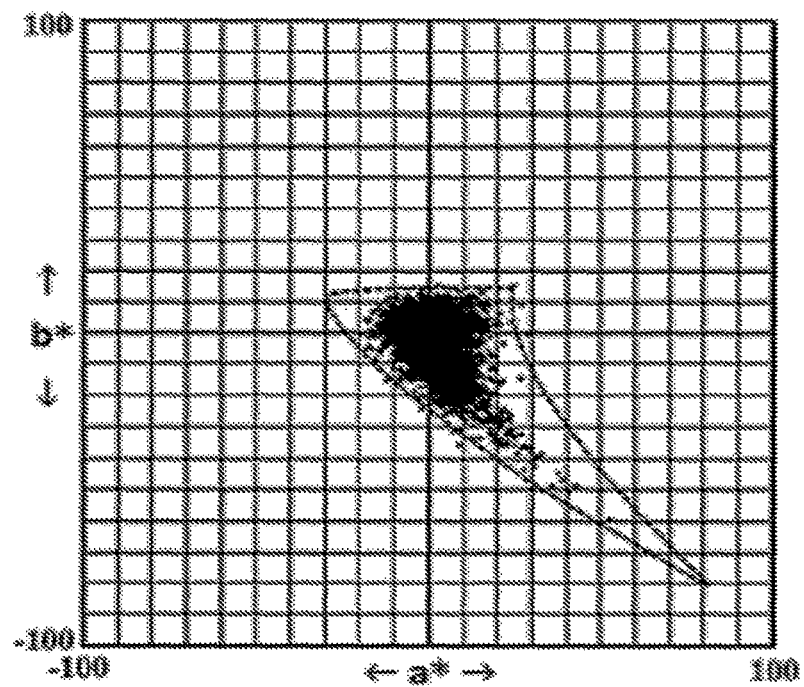
FIG. 21 is a diagram illustrating distributions on L*-a* and a*-b* surfaces at L*=15.

Spectroscopic means used for measurement needs to have a wavelength resolution appropriate to an object to be measured. Interference effect materials, which are often used today, have a sharp reflectance and a reflection property close to a saturated color which is a single-wavelength color. Accordingly, measured glittering reflections are distributed in a wide range in the color space. Therefore accurate measurement cannot be performed by a measurement method such as an RGB method, which has a limited color gamut. FIG. 20 illustrates an example of measurement of interference effect materials. In this example of measurement, results of measurements on a product named Xirallic Crystal Silver from Merck KGaA are shown. When glittering reflection in a small region enclosed in a rectangle is displayed, a spectral reflectance factor measured has a sharp and narrow shape as a function of wavelength. A region of the lightest color that indicates a marginal domain of the object color and distributions were compared. Values in the CIELAB color space using artificial illuminant D65 at an observation view field of 10° were calculated from the measured spectral reflectance factors. FIG. 21 illustrates a distribution in L*-a* and a*-b* surfaces at L*=15 together with the lightest color region. It is shown that the results of the measurement are distributed to near the lightest color. Therefore measurements need to be made with a wavelength resolution that is sufficient for measuring a wide region.

(Two-Dimensional Image Sensor for Image Taking)

A two-dimensional image sensor for image taking will be described below.

Special interference effect materials are often used in automobile coating today. The interference effect materials contain glittering reflection colors that are very fine and bright and have a wide color representation range. Multi-angle information is effectively used for such paint colors. In order to perform accurate image analysis calculations for evaluating features, measurement with a high resolution, high precision, high dynamic range and a wide color gamut over an entire image is needed. Therefore, a monochrome two-dimensional image sensor 4 is used in embodiments of the present invention to prevent occurrence of a moire image and the spectroscopic means is provided in a stage before the image pickup to implement a mechanism that acquires spectral information in a wide color gamut for every pixel.

The two-dimensional image sensor 4 preferably includes an anti-blooming mechanism for identifying a good glittering reflected color with a high precision. If the two-dimensional image sensor 4 is a CCD image pickup sensor, it is desirable that the image sensor include means for preventing occurrence of noise in long time exposure by using a Peltier cooling device, a water cooling mechanism, an air cooling mechanism or a combination of these. The two-dimensional image sensor 4 has a dynamic range of 8 bits or greater, preferably 16 bits or greater in output resolution. Furthermore, it is desirable that the device include an anti-blooming mechanism.

The two-dimensional image sensor 4 is preferably does not include a parallel arrangement of color RGB elements in order to prevent occurrence of false colors or moire in measurement in a minute region. Monochrome sensors do not cause such problems. There are devices that are capable of RGB measurement but do not rely on a parallel arrangement. Such devices do not produce false colors and are effective in measurement of small reflection from glitter additive to be particularly measured by the present invention. RGB image pickup devices that do not rely on a parallel arrangement include three-CCD sensors and Foveon sensors.

Figure 22:
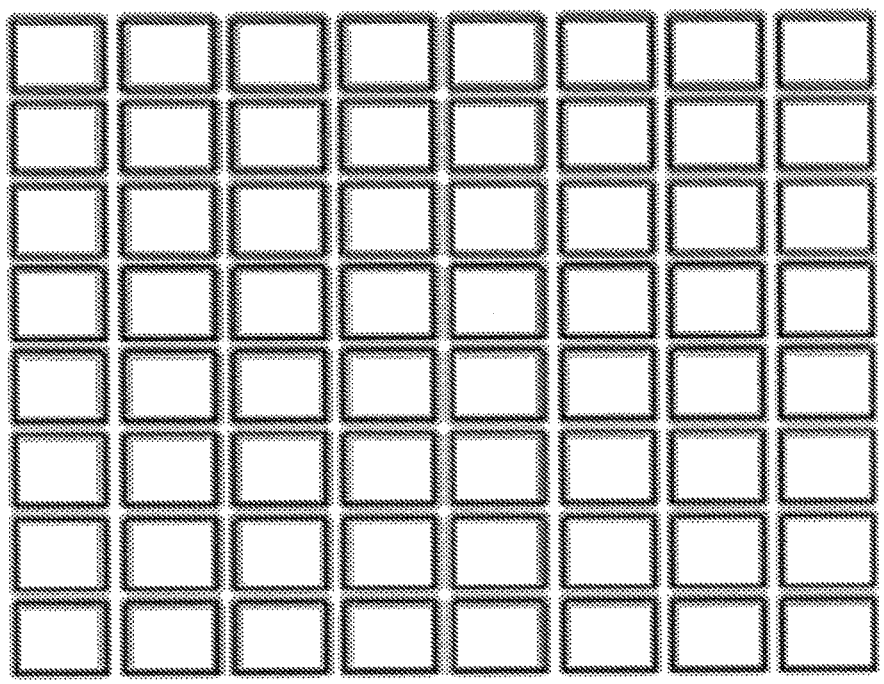
FIG. 22 is a diagram illustrating a monochrome two-dimensional image sensor.
Figure 23:
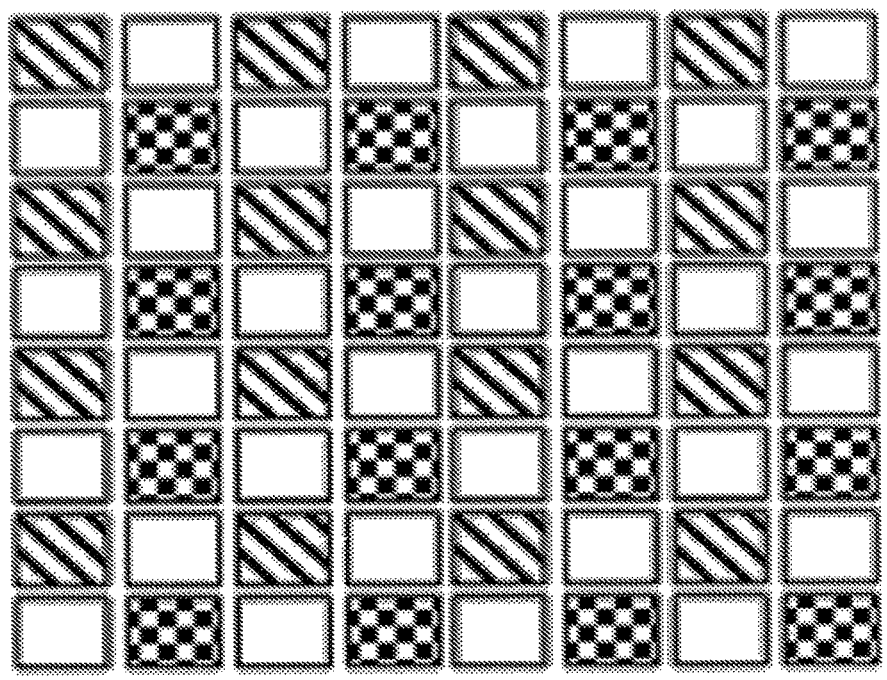
FIG. 23 is a diagram illustrating a Bayer-arrangement two-dimensional image sensor.
Figure 24:
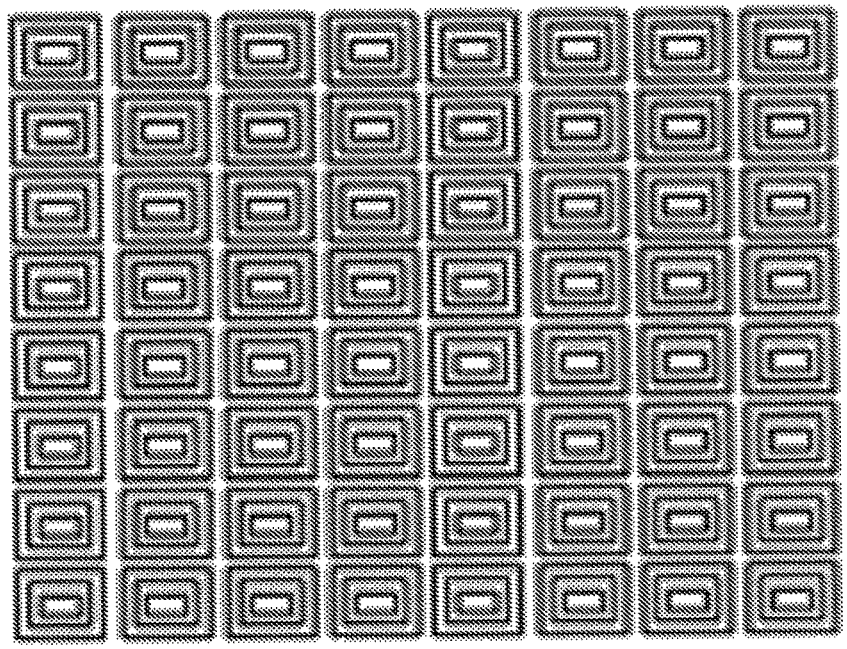
FIG. 24 is a diagram illustrating a Foveon two-dimensional image sensor.
Figure 25:
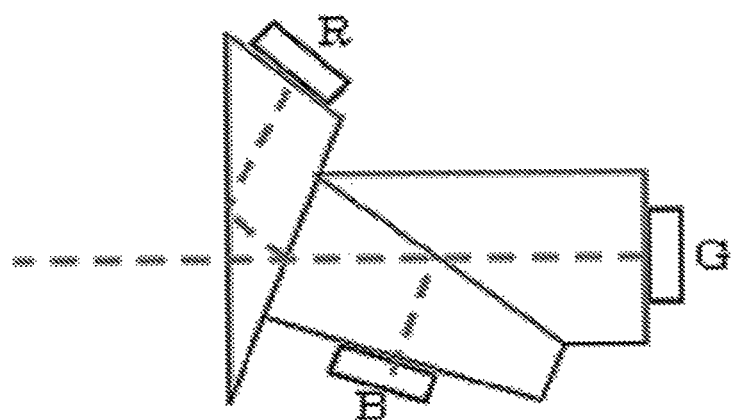
FIG. 25 is a diagram illustrating a three-CCD two-dimensional image sensor.

FIGS. 22 to 25 illustrate several types of two-dimensional image sensors. FIG. 22 illustrates a monochrome image sensor, FIG. 23 illustrates a Bayer-arrangement color image sensor, FIG. 24 illustrates a Foveon color image sensor, and FIG. 25 illustrates a three-CCD two-dimensional image sensor. In the case of the Foveon image sensor in FIG. 24, one pixel has R, G, B sensitivities. The monochrome two-dimensional image sensor in FIG. 22 is most efficient, and allows measurement with a high sensitivity. The Foveon color image sensor in FIG. 24 and the three-CCD two-dimensional image sensor in FIG. 25 do not use a parallel pixel arrangement and are capable of fast measurement. On the other hand, the Bayer arrangement color image sensor in FIG. 23 uses a parallel pixel arrangement, which can have adverse effects such as changes in geometrical conditions and occurrence of false colors.

(Optical Lens)

The optical lens 8 for image formation disposed before the monochrome two-dimensional image sensor 4 is preferably an optical lens with a high resolution, low distortion near the rim and low attenuation and preferably has a field angle of less than 40° in order to minimize image distortion near the rim. For illumination, a mechanism capable of switching between at least two angles is provided to enable measurement at multiple aspecular angles (see FIGS. 1, 3 and 4).

(Spectral Imaging)

Spectral imaging for acquiring spectral information for all image pickup pixels will be described below.

The spectroscopic means 6 provided immediately before the optical lens 8 may include a plurality of band-pass filers having different pass bands according to measurement wavelengths as illustrated in FIG. 1 and switching may be made from one filter to another to take images, thereby acquiring spectral information. In this case, if measurement is made at every 10 nm in the range between 400 nm to 700 nm, which is a visible light range, 31 band-pass filters are provided and switching is made from one filter to another while repeating image taking at the same position to acquire 31 pieces of spectral information for all pixels.

Here, the spectroscopic means 6 only needs to disperse light incident on the two-dimensional image sensor 2 and may be disposed before the optical lens 8 or in a midway position between the optical lens 8 and the two-dimensional image sensor 2, or immediately before the two-dimensional image sensor 2.

Figure 26:
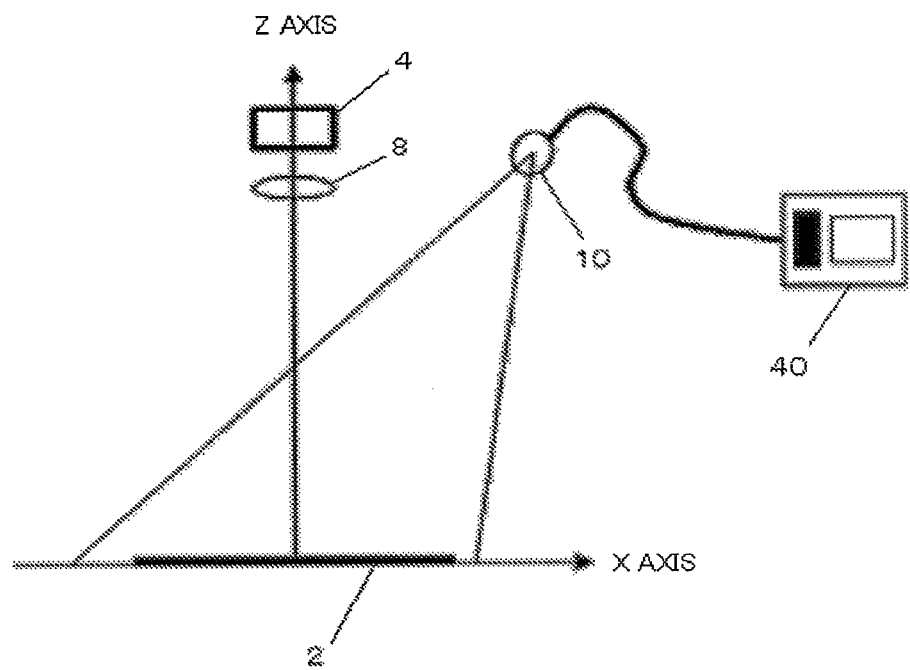
FIG. 26 is a diagram illustrating an example in which spectroscopic means is used at the illumination side.

Another way of providing spectroscopic means at the illumination side is to use spectroscopic means at the illumination side as illustrated in FIG. 26 to apply a monochromatic light to a sample surface. Means for producing monochromatic light may be a spectral light source device 40 that uses a white light illuminant having radiation energy that is sufficient for a desired wavelength range in which spectral information is to be acquired in combination with a reflective diffraction element, a transmission diffraction element, a prism or the like, or a spectral light source device in which a plurality of interference filters that filters light incident on a spectral device are replaced with one another, or a liquid-crystal tunable filter or a combination of band-pass filter such as AOTFs are used, or switching is made between single-wavelength illumination light sources. In addition, a mechanism is provided that uses one of or a combination of a lens, a mirror, or optical fiber and the like so that an illumination position and a light distribution pattern does not change while spectroscopically changing wavelength. For receiving light, a combination of two-dimensional monochrome image pickup devices or two-dimensional color image pickup devices is used.

Figure 27:
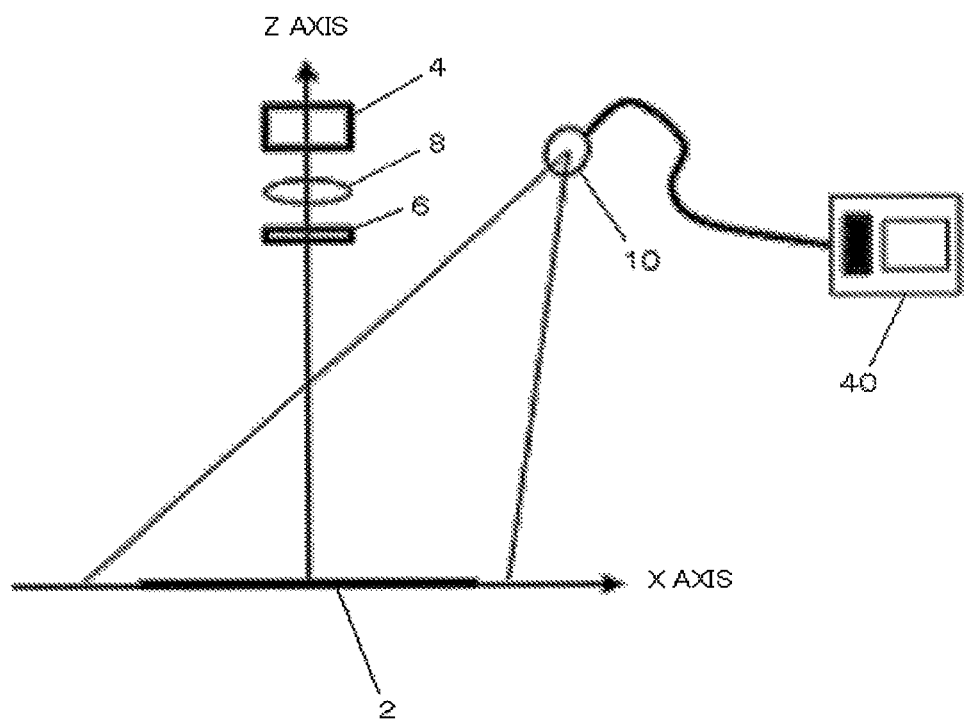
FIG. 27 is a diagram illustrating an example in which spectroscopic means is used at the illumination side and the light receiving side.

Furthermore, spectroscopic means may be used at both of the illumination side and the light reception side as illustrated in FIG. 27. This can be used as a bispectral multi-angle spectral imaging apparatus to apply light to a fluorescent object. In this case, the spectroscopic means 6 only needs to disperse light incident on the two-dimensional image sensor 2 and may be provided before the optical lens 8, in a midway position between the optical lens 8 and the two-dimensional image sensor 2, or immediately before the two-dimensional image sensor 2.

(Lighting Device)

A light source lamp such as a tungsten lamp, a halogen lamp, a xenon lamp, or a white LED with a mechanism such as optical fiber and a light guide or a light source lamp with a mirror, a projection lens and the like that is capable of illuminate the sample surface 2 to be measured and the white reference surface 12 at the same time may be used as the lighting device 10. If the light distribution pattern or the spectral distribution provided by the lighting device 10 varies with changes in temperature, it is desirable to provide an appropriate cooling mechanism using Peltier cooling, water cooling, air cooling or a combination of these.

Figure 28:
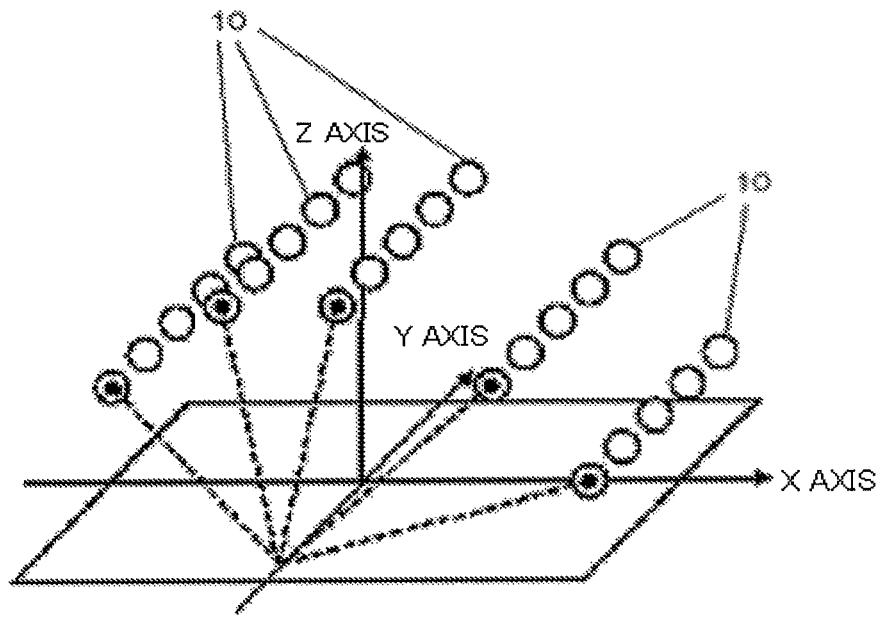
FIG. 28 is a diagram illustrating an arrangement of a plurality of lighting devices.

A specific configuration of the lighting device will now be described. FIG. 28 is a diagram illustrating an arrangement of a plurality of illuminants. As illustrated in FIG. 28, the plurality of lighting devices 10 are arranged along the zenith angle direction and the azimuth angle direction or the Y axis direction, so that a point-like or linear illumination pattern can be provided from a plurality of angles without provision of a moving member.

Figure 29:
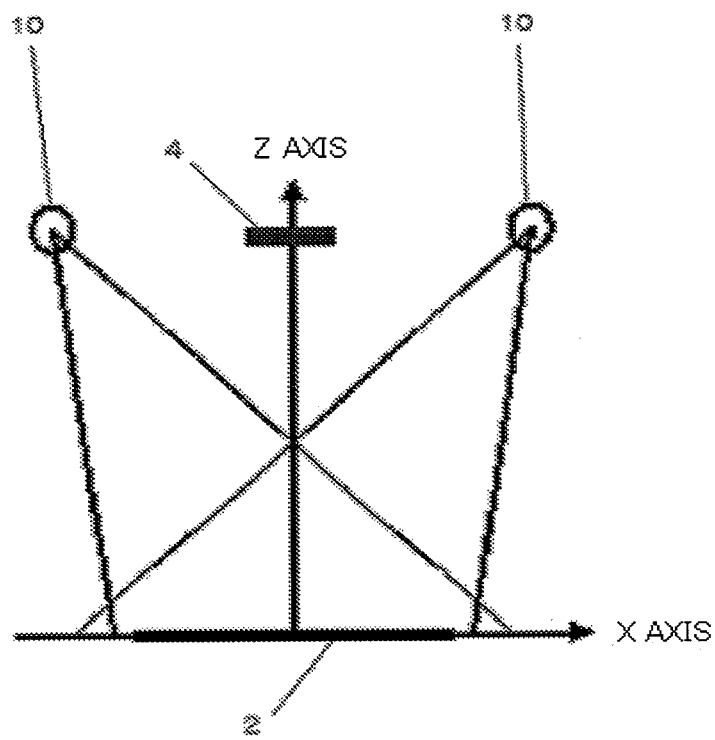
FIG. 29 is a diagram illustrating a state in which light sources placed symmetrically with respect to a vertical axis from the center of a sample surface are lit at the same time.

In addition, a combination of a plurality of illuminants can be lit at the same time to provide a wide variety of optical geometrical conditions and change spatial distributions of light sources. Furthermore, shadowless diffused illumination conditions can be produced by lighting light sources at positions that are symmetric with respect to the axis (the Z axis) perpendicular to the center of the sample surface as illustrated in FIG. 29.

By using various patterns of lighting for measurement of the same sample in this way, simulation calculations can be performed to acquire a various kinds of information, thereby measurement time and the number of measurement times can be reduced.

Furthermore, by lighting a plurality of light sources at the same time to provide a sufficient amount of light, precise, short-time and fast measurement can be performed on a low-reflectance object to be measured.

(Configuration of Apparatus)

Figure 30:
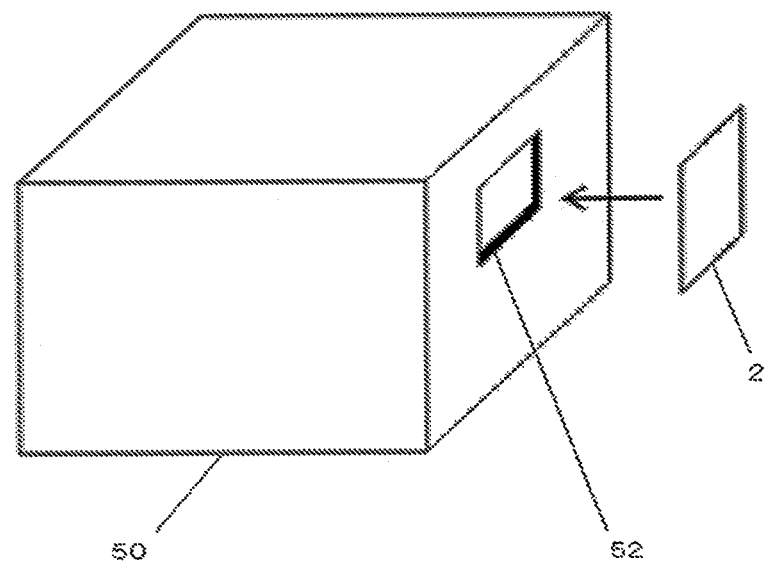
FIG. 30 is a diagram illustrating an exemplary configuration of a measurement apparatus.

In an example configuration of the measurement apparatus, the apparatus is contained in a rectangular housing 50 having a measurement window 52 in one face for placing a sample to be measured as illustrated in FIG. 30 so that the sample 2 can be brought into contact with and fixed on the housing 50 from the outside. By changing the orientation of the housing 50 to position the measurement window at the top to allow measurement of a large sample or to position the measurement window at the bottom to allow contactless measurement of a liquid sample, a viscous sample, cosmetics and the like.

Figure 31:
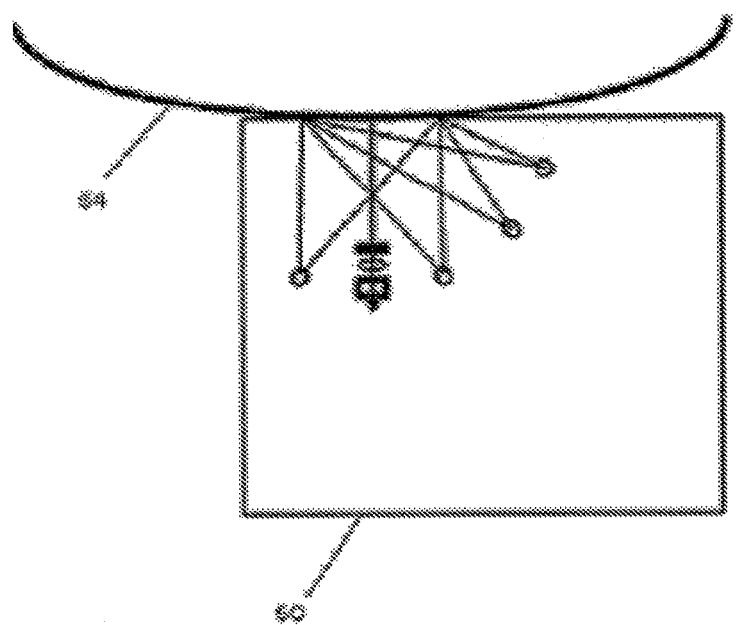
FIG. 31 is a diagram illustrating an example in which a large sample such as a fender or a door is measured.

When the measurement window 52 is positioned at the top as illustrated in FIG. 31, measurement of a large sample 54 such as a fender or a door can be easily made. Furthermore, measurement of powder or liquid in a glass cell can be made.

Figure 32:
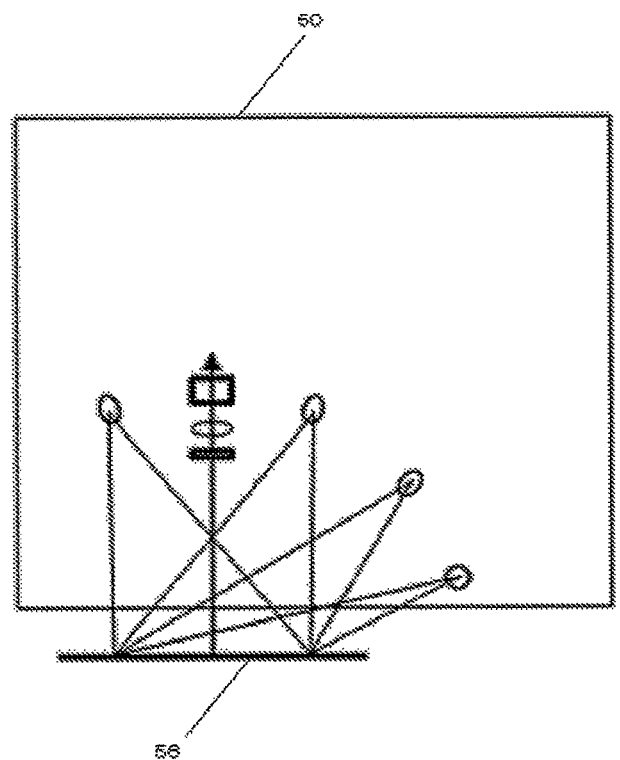
FIG. 32 is a diagram illustrating an example in which a liquid sample or the like is measured.

On the other hand, when the measurement window is positioned at the bottom as illustrated in FIG. 32, contactless measurement of a sample 56 such a liquid sample, a viscous sample, powder, cosmetics or the like can be made. In addition, contactless measurement of a human organism and skin can be effectively made. This enables measurement of a translucent human organism without influence of changes in blood flow due to pressure or edge loss errors.

(Method of Calibrating Devices)

Figure 5:
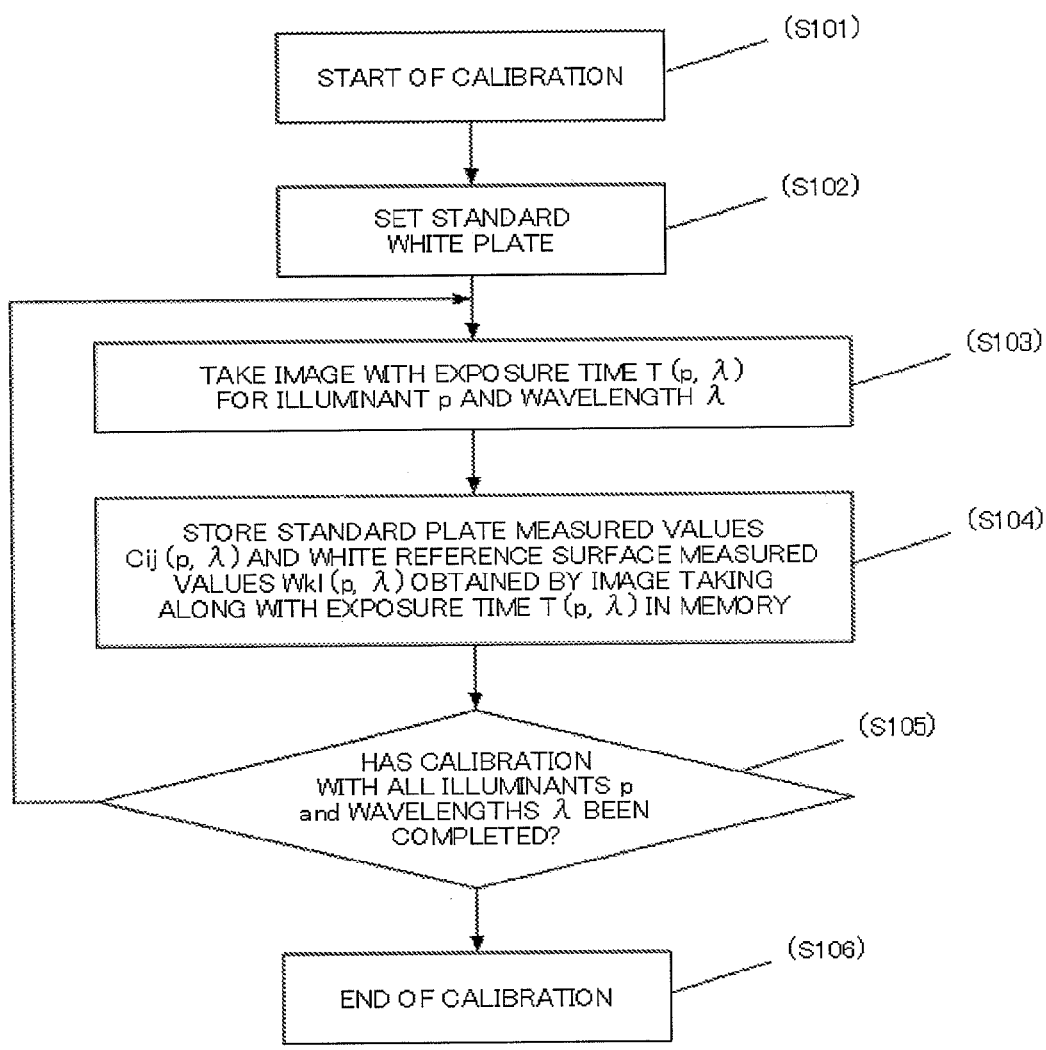
FIG. 5 is a flowchart illustrating a calibration procedure of the present invention.
Figure 6:
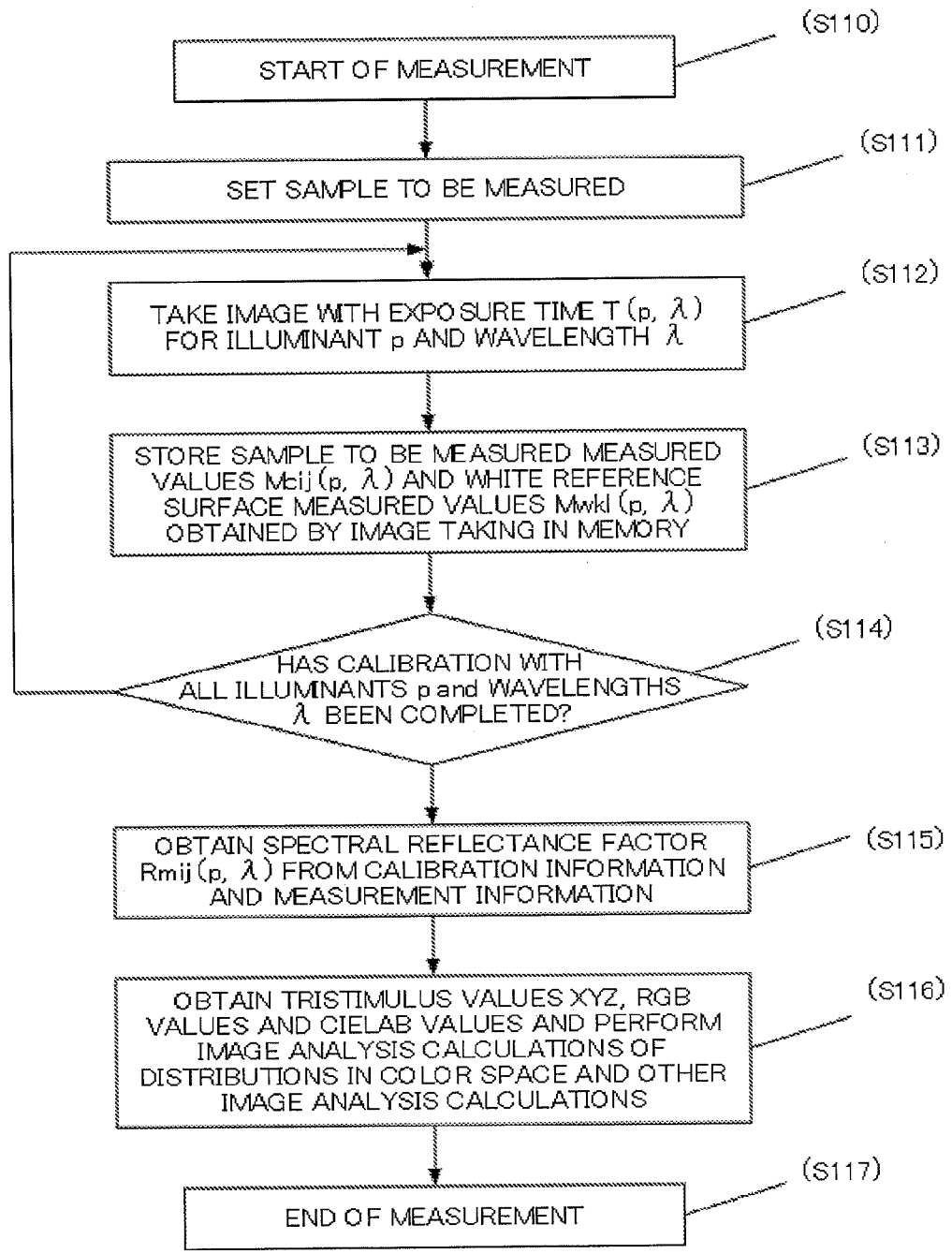
FIG. 6 is a flowchart illustrating a measurement procedure of the present invention.

A method for calibrating devices performed before actual measurement, and a method for measurement and image analysis calculations performed after the calibration will be described below with reference to FIGS. 5 and 6. First, the method for calibrating the devices will be described with reference to FIG. 5.

For stable measurement, it is important to establish calibration means. Calibration is performed in order to address environmental changes such as temperature and humidity changes, instability of power supply, and changes in the light source devices and optical devices over time. Calibration is performed immediately after power-on the apparatus or several hours or days after the last calibration to make corrections so that measured values always fall within a certain error margin.

First, a standard white plate for reference is provided (S102). The surface structure is a lusterless diffusing surface and is uniform in a measurement range. It is desirable that the spectral reflectance factor of the surface structure is approximately 80% or greater in a measurement wavelength region. A typical standard white plate is a plate made of pressed barium sulfate powder. The spectral reflectance factor of the standard white plate at a wavelength $\lambda$ is measured beforehand with another calibrated spectrophotometer and is stored in a memory. The measured value is denoted by $R_c(\lambda)$. The standard white plate is placed in place of a sample to be measured, an image of the standard white plate is taken at every measurement wavelength in illumination p, and the results are recorded in the memory. Each of the values is denoted by $C_{ij}(p, \lambda)$, where (i, j) represents the position of a pixel in an image of the standard white board taken.

At the same time, an image of the white reference surface provided around the standard white plate is also taken and recorded. Each of the values is denoted by $W_{kl}(p, \lambda)$, where (k, l) represents the position of a pixel in an image of the white reference surface taken. Desirably, the surface structure of the white reference surface is a lusterless diffusing surface that is as much independent of light reception and illumination angles as possible. It is also desirable that the spectral reflectance factor of the white reference surface is approximately 80% or greater in a measurement wavelength region. Since properties of the spectroscopic means 6 and spectral distributions of the lighting devices 10 range vary in the measurement wavelength, exposure time may be optimized according to each measurement wavelength in order to correct the changes before calibration information is measured (S103, S104). When the calibration with the plurality of illuminants and different wavelengths are completed, the calibration process ends (S105, S106). At this time, the exposure times are stored along with the calibration information. When measurement of a sample is made, the measurement is performed with the same exposure times that are stored here. By using the values obtained by taking pictures of the white reference surface, variations from location to location of the surface measured due to instability of power supply and changes in the light source devices and optical devices over time can be corrected. By controlling exposure time, spectral distributions of different light sources, the spectral properties of the spectroscopic means, and the spectral sensitivity of the image pickup devices that vary with different measurement wavelengths can be made constant to ensure a high dynamic range.

The calibration method will be described in further detail with reference to FIG. 2.

The white reference surface 12 is set around a sample surface 2 to form a double-beam optical system. In one example configuration, the white reference surface 12 is disposed inside the measurement window. The white reference surface 12 and the white calibration plate 3 placed in the sample setting location are measured at the same time to obtain a calibration coefficient at that point in time. Since two-dimensional image pickup devices are used, images of different regions of the white reference surface 12 and the sample surface 2 are taken at the same time. The values of the results of the image taking of the white reference surface 12 are stored in the memory.

A standard white diffusion surface to which values are assigned or an alternative white surface with which the standard white diffusion surface can be referred to is used in calibration. The surface is referred to as the white calibration plate 3. During calibration, the white calibration plate 3 and the white reference surface 12 are measured at the same time to obtain calibration coefficients $C_I(x, y, \lambda)$. The subscript I represents the type (position) of an illuminant. The calibration coefficients can be obtained based on a level setting that takes into consideration the range of spectral reflectance factors that are possible in measurement.

The level setting is a setting that associates an output count value from the two-dimensional image pickup device with a spectral reflectance factor of the white calibration plate 3. For example, if the spectral reflectance factor of the white calibration plate is 90% for an image pickup device capable of 16-bit output and 90% is associated with an output count value of 30000, then the maximum measurable spectral reflectance factor is 90×65535/30000=196.6%.

Figure 33:
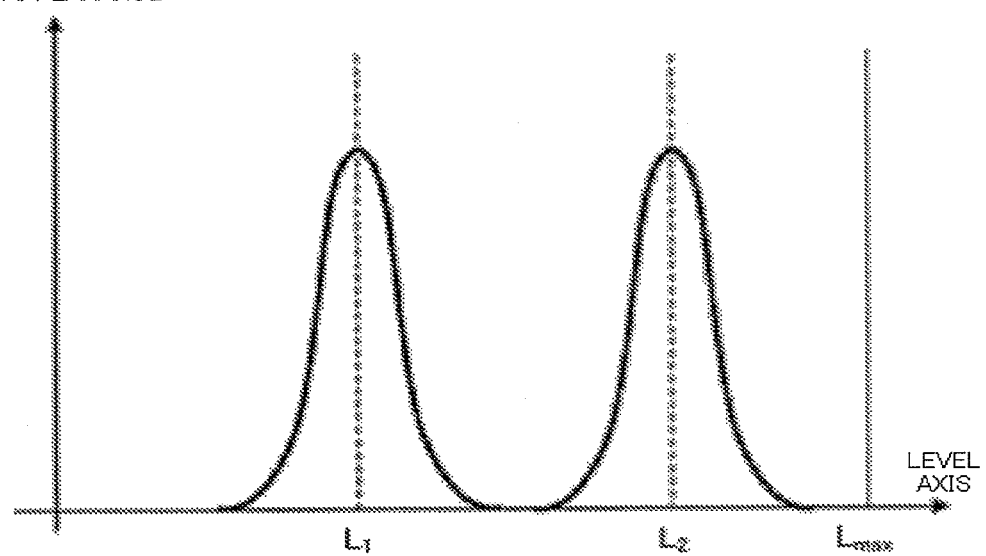
FIG. 33 is a diagram illustrating the frequency of appearance at different levels for explaining calibration coefficients.

Calculation of a calibration coefficient will be described with reference to FIG. 33.

(1) The spectral reflectance factor of a standard white diffusion surface provided beforehand or an alternative white surface with which the standard white diffusion surface can be referred to is denoted by $R_W$. The white calibration plate 3 has a uniform surface and the spectral reflectance factor $R_W$ does not change with optical geometrical conditions or regions.

(2) Likewise, the spectral reflectance factor of the white reference surface 12 is denoted by $R_R$. The reference surface has a uniform surface and the spectral reflectance factor $R_R$ does not change with optical geometrical conditions or regions.

(3) The maximum value output from an image pickup device is denoted by $L_{max}$ and the level setting value at illumination I for the white calibration plate 3 is denoted by $L_I$ ($0 < L_I < L_{max}$).

(4) Exposure time and the amount of light are adjusted so that the position of the distribution of output values $V_I(x, y, \lambda)$ from the image pickup device at illumination I and wavelength $\lambda$ is substantially peaked at the position of $L_I$ (the adjustments will be described later).

(5) The white calibration plate 3 and the white reference surface 12 are measured at the same time. The white calibration plate measured value is denoted by $V_{I,W}(x_W, y_W, \lambda)$ and the white reference surface measured value is denoted by $V_{I,R}(x_R, y_R, \lambda)$. Here, $(x_W, y_W) \neq (x_R, y_R)$. The white reference surface measured value $V_{I,R}(x_R, y_R, \lambda)$ is stored in the memory. This is used for correction during measurement.

(6) The calibration coefficient for calculating the spectral reflectance factor for a part of a sample to be measured at illumination I and wavelength $\lambda$ is $$C_I(x_W, y_W, \lambda) = R_W / V_{I,W}(x_W, y_W, \lambda).$$

During calibration, the exposure time of the two-dimensional image pickup device is changed according to measurement wavelength and a difference in the light amount of the light source, a difference in the efficiency of the spectroscopic means (a difference in transmittance or the like), and a difference in the spectral sensitivity of the image pickup device at the wavelength are corrected to ensure a high dynamic range.

In addition, exposure time is multiplexed, like setting short-exposure time and long-exposure time, to extend the dynamic range. Exposure time is multiplexed by multiplexing level setting or providing a low-reflectance calibration plate (gray or black or the like).

Adjustment of the exposure time during calibration is automatically optimized by computer control based on the distribution of measurement count values during the calibration. Exposure time can be adjusted manually as well.

A method for extending the dynamic range other than multiplexing the exposure time is to multiplex the light amount of illumination. In this case, electrical energy supplied to the illuminant or the number of illuminants may be multiplexed. In addition, the calibration plate described above may be replaced or the level setting may be changed.

Moreover, multiplexing of exposure time and multiplexing of the light amount of illumination may be combined.

During measurement, the sample surface 2 and the white reference surface 12 are measured at the same time with the exposure time optimized for each wavelength, the measured values are compared with the measured count values of the white reference surface recorded during calibration, and correction is made. Changes to be corrected include changes in the light amount of illumination, changes in the spectroscopic means (for example changes in the efficiency of dispersion due to changes in transmittance of a filter), changes in the sensitivity of a two-dimensional image pickup device, errors in exposure time (especially in short-time exposure) and the like. The white reference surface measured values $V_{I,R}(x_R, y_R, \lambda)$ at illumination I and wavelength $\lambda$ at the time of calibration have been stored in the memory. While an example measurement method will be described below, the method for interpolation calculation of a time correction coefficient for a sample surface is not limited to this; various methods such as two-dimensional spline interpolation may be used.

A method for interpolation calculation of a time correction coefficient for a sample surface 2 will be described. White reference surface measured value being measured is denoted by $V_{I,RM}(x_R, y_R, \lambda)$. The time correction coefficient with respect to the time of calibration is $$F_I(x_R, y_R, \lambda) = V_{I,RM}(x_R, y_R, \lambda) / V_{I,R}(x_R, y_R, \lambda) \quad \text{[Expression 14]}$$

The range of $X_R$ is $X_b \leq x_R \leq x_e$ and the range of $y_R$ is $y_b \leq y_R \leq y_e$. Consider interpolation at point $P(x_p, y_p)$. First, linear interpolation is performed in the Y axis direction. In this case, $$F_0 = F_I(x_p, y_b, \lambda) \cdot [(y_e - y_p)/(y_e - y_b)] + F_I(x_p, y_e, \lambda) \cdot [(y_p - y_b)/(y_e - y_b)] \quad \text{[Expression 15]}$$

Then, a displacement from the liner interpolation along the Y axis is calculated for $x_b$ and $x_e$.

$$\Delta F_{xb} = F_I(x_b, y_p, \lambda) - F_I(x_b, y_b, \lambda) \cdot [(y_e - y_p)/(y_e - y_b)] - F_I(x_b, y_e, \lambda) \cdot [(y_p - y_b)/(y_e - y_b)]$$

$$\Delta F_{xe} = F_I(x_e, y_p, \lambda) - F_I(x_e, y_b, \lambda) \cdot [(y_e - y_p)/(y_e - y_b)] - f_I(x_e, y_e, \lambda) \cdot [(y_p - y_b)/(y_e - y_b)] \quad \text{[Expression 16]}$$

The displacement is obtained for each illumination condition.

The time correction coefficient for each illumination condition is denoted by $F_{ij}(I, \lambda)$. Here, the subscripts ij represent a position on the white reference surface (which is the same as the position on a sample surface) corresponding to $x_R, y_R$ in the formula given earlier.

(Measurement of Actual Sample Surface to be Measured)

An actual measurement method will be described with reference to FIG. 6. A sample to be measured is set (S111), an image is taken with each measurement wavelength (S112) and the result is recorded in a memory (S113). The value is denoted by $V_{Mij}(I, \lambda)$. In addition, $F_{ij}(I, \lambda)$ described above is obtained from a measured value of the image of the white reference surface taken at the same time. In this case, the spectral reflectance factor $R_{ij}(I, \lambda)$ of the sample to be measured after calibration can be obtained according to Formula 17. Here, the calibration coefficient for the illumination I is $C_{ij}(I, \lambda)$. When these calculations are completed for a plurality of illumination conditions and different wavelengths, the measurement ends (S114).

$$R_{ij}(I, \lambda) = V_{Mij}(I, \lambda) \cdot C_{ij}(I, \lambda) / F_{ij}(I, \lambda) \quad \text{[Expression 17]}$$

In this case, a pixel position on the white reference surface is obtained by referring to a position that effectively works on a pixel position (i, j) on the sample surface to be measured for which correction is made, for example a position on the white reference surface that intersects with a line drawn from a position to be measured in parallel to the X axis and with a line drawn from the position in parallel to the Y axis as an extrapolation position for the X axis and the Y axis or applying partial interpolation and averaging. Measurement of the white reference surface is made at the same time as the time of image taking and measured values are used for correction for accommodating changes in the light amount of illumination and changes and errors in exposure time of an image pickup device during measurement. This enables high-precision and stable measurement. Note that a light trap or a standard black plate may be used in measurement of calibration data to make corrections to spectral reflectance factors near 0.

Figure 34:
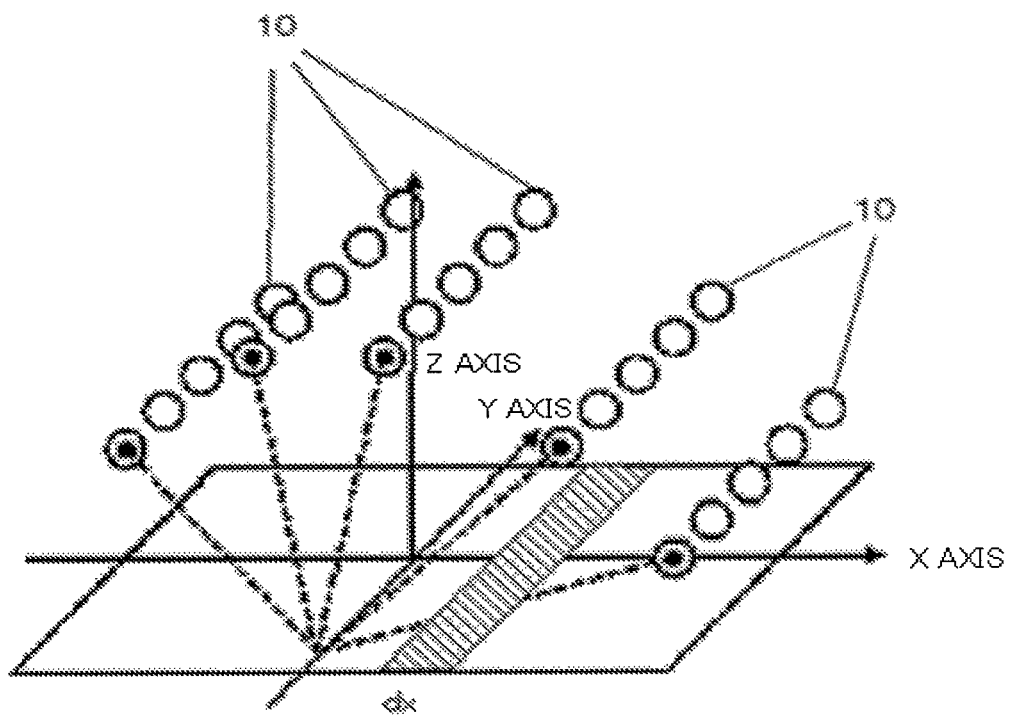
FIG. 34 is a diagram illustrating a position at which measured values can be considered identical when a linear light source is used.

Depending on measurement positions in an image, there are regions for which optical geometrical conditions can be considered to be the same. Examples of such regions are a region along the Y axis that has a width dx along the X axis, as depicted in FIG. 34 (the shaded region) when linear light sources are used and a small region where changes in optical geometrical conditions are negligible. In that case, image information under substantially identical optical geometrical conditions can be obtained and can be used as information for obtaining distributions in a color space and feature quantities in an image.

Figure 35:
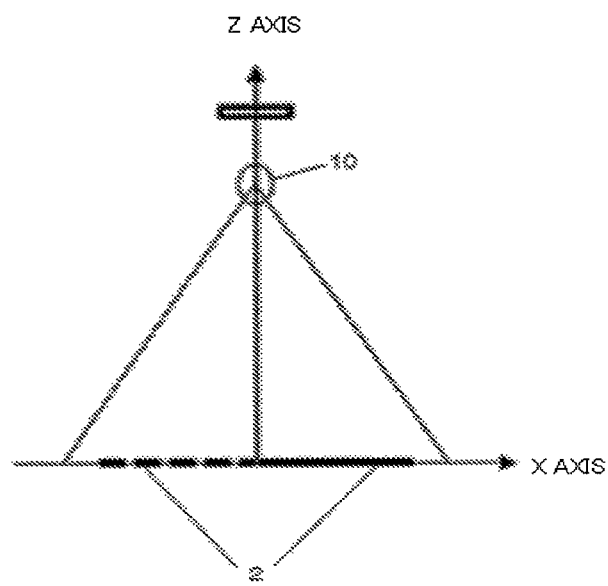
FIG. 35 is a diagram illustrating a position at which measured values can be considered identical when a point light source is used.
Figure 36:
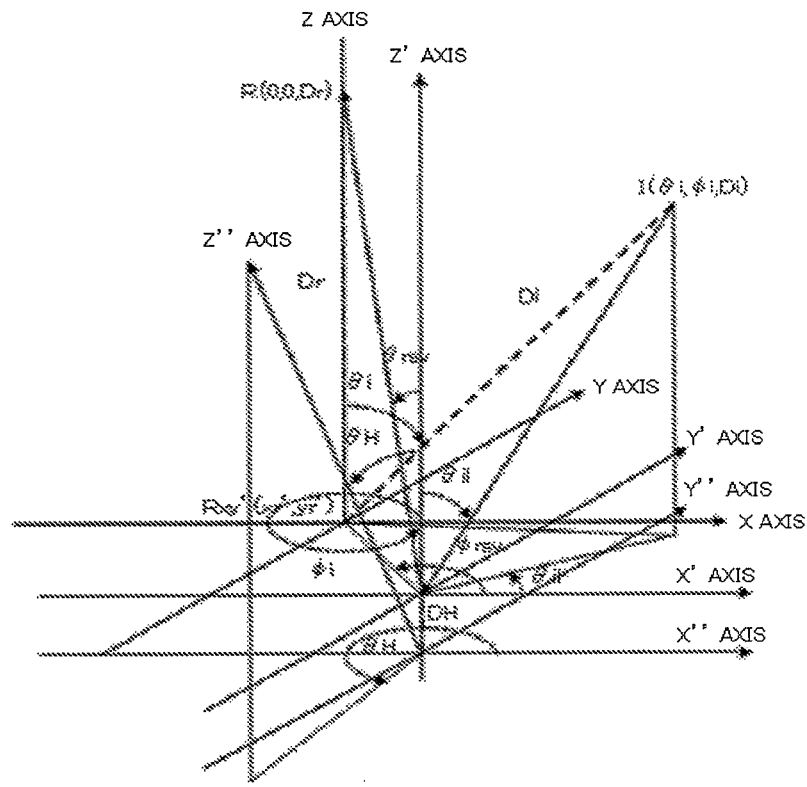
FIG. 36 is a diagram illustrating a three-dimensional curved surface measurement.

Depending on the relationship between a measurement position in an image and illumination, there are regions for which optical geometrical conditions can be considered to be symmetric azimuth angles. For example, when a point light source is used as illustrated in FIG. 35, such a relationship is the relationship between illumination displaced from the center of the illuminant in the + direction along the Y axis and illumination displaced from the center of the illuminant in the same direction along the Y axis or the relationship between illumination displaced from the center of the illuminant in the—direction with respect to the Y axis and illumination displaced in the—direction with respect to the Y axis. In this case the orientation of effect materials can be measured.

(Methods for Calculating Feature Quantities by Image Analysis)

Methods for calculating feature quantities by image analysis using measured spectral imaging information will be described below. The calculation methods are illustrative only. Since measurements in the present invention are performed with high resolution, high precision for every pixel and many types of image analysis calculations can be used and high reliability of the results of the calculations can be ensured.

A method for obtaining the average of measured spectral reflectance factors $R_{mij}(p, \lambda)$ for all pixels with each illuminant with respect to multi-angle information will be described (S115). The aspecular angle differs from pixel position (i, j) to pixel position. The average $R_m(p, \lambda)$ of spectral reflectance factors can be written as Formula 18.

$$R_m(p, \lambda) = \Sigma\Sigma R_{mij}(p, \lambda)/N \quad \text{[Expression 18]}$$

Here, $\Sigma$ is calculated for the region from the i-th pixel to the i+I-th pixel in the X axis direction and the region from the j-th pixel to the j+J-th pixel in the Y axis direction. N is the number of pixels included in a calculation region and $N=(I+1)\cdot(J+1)$.

The average aspecular angle $\theta(p)$ for the calculation region can be written as Formula 19.

$$\theta(p) = \Sigma\Sigma\theta_{ij}(p)/N \quad \text{[Expression 19]}$$

The average spectral reflectance factor $R_{mij}(p, \lambda)$ can be obtained at any aspecular angle $\theta(p)$ for a desired spatial resolution can be obtained by choosing i, j, I and J appropriately. When I and J are chosen to be small, changes in aspecular angle $\theta(p)$ in the average calculation region will be small and the average can be calculated with a high spatial resolution. On the other hand, when I and J are chosen to be large, the spatial resolution will decrease but the effects of averaging and smoothing will be high because N is large.

Parameters such as lightness distributions for different angles, color spatial distributions, spatial distribution for each image position, the number of appearing colors, information entropy, and image filters, fractal dimensions and other parameters can be calculated and displayed as obtained multi-angle spectral image information.

Furthermore, based on the information mentioned above, reproduction information can be provided by computer graphics.

(Method for Obtaining Color Values)

A method for obtaining color values from spectral reflectance factors $R_{mij}(p, \lambda)$ of all of the measured pixels will be described (S116). In the procedure for calculating color values, tristimulus values XYZ are calculated first. A typical method established by Comission Internationale de l'Eclairage (CIE) is used.

The tristimulus values $X_{ij}(p)$, $Y_{ij}(p)$, $Z_{ij}(P)$ of each pixel can be written as Formula 20.

$$X_{ij}(p) = k\int P(\lambda)x(\lambda)R_{mij}(p,\lambda)d\lambda$$

$$Y_{ij}(p) = k\int P(\lambda)y(\lambda)R_{mij}(p,\lambda)d\lambda$$

$$Z_{ij}(p) = k\int P(\lambda)x(\lambda)R_{mij}(p,\lambda)d\lambda$$

$$K = 100/\int P(\lambda)y(\lambda)d\lambda \quad \text{[Expression 20]}$$

Here, $P(\lambda)$ represents a spectral distribution of illumination light that is possible when an object is observed and the range of wavelengths $\lambda$ to be integrated is a visible light region used in the measurement. When presented on a computer display or a printer, the tristimulus values $X_{ij}(p)$, $Y_{ij}(p)$, $Z_{ij}(P)$ are converted to $R_{ij}(p)$, $G_{ij}(p)$, $B_{ij}(P)$ values. Methods for converting to sRGB and Adobe RGB based on standards are known.

As in the calculations of the average of spectral reflectance factors described above, the average of tristimulus values can be obtained according to Formula 21.

$$X(p) = \Sigma\Sigma X_{ij}(p)/N$$

$$Y(p) = \Sigma\Sigma Y_{ij}(p)/N$$

$$Z(p) = \Sigma\Sigma Z_{ij}(p)/N \quad \text{[Expression 21]}$$

A method for obtaining color values from the tristimulus values $X_{ij}(p)$, $Y_{ij}(p)$, $Z_{ij}(p)$ of all pixels measured will be described. A typical method is to obtain L*a*b* which are values in the CIELAB color space specified in CIE by using Formula 22.

$$L^*_{ij}(p) = 116 f(Y_{ij}(P)/Y_n) - 16$$

$$a^*_{ij}(P) = 500\{f(X_{ij}(p)/X_n) - f(Y_{ij}(p)/Y_n)\}$$

$$b^*_{ij}(p) = 200\{f(Y_{ij}(p)/Y_n) - f(Z_{ij}(p)/Z_n)\} \quad \text{[Expression 22]}$$

Here,
when $X_{ij}(p)/X_n > 0.00856$, $f(X_{ij}(p)/X_n) = (X_{ij}(p)/X_n)^{1/3}$ when $X_{ij}(p)/X_n < 0.00856$, $f(X_{ij}(p)/X_n) = 7.787 (X_{ij}(p)/X_n) + 16/116$
when $Y_{ij}(p)/Y_n > 0.00856$, $f(Y_{ij}(p)/Y_n) = (Y_{ij}(p)/Y_n)^{1/3}$ when $Y_{ij}(p)/Y_n < 0.00856$, $f(Y_{ij}(p)/Y_n) = 7.787 (X_{ij}(p)/X_n) + 16/116$ when $Z_{ij}(p)/Z_n > 0.00856$, $f(Z_{ij}(p)/Z_n) = (Z_{ij}(p)/Z_n)^{1/3}$ when $Z_{ij}(p)/Z_n < 0.00856$, $f(Z_{ij}(p)/Z_n) = 7.787(Z_{ij}(p)/Z_n) + 16/116$ $X_n$, $Y_n$, and $Z_n$ are tristimulus values obtained by measurement of an object having a spectral reflectance factor of 100%. As in the calculation of the average of spectral reflectance factors described above, the average of CIELAB values can be obtained according to Formula 23.

$$L^*(p) = \Sigma\Sigma L^*_{ij}(p)/N$$

$$a^*(p) = \Sigma\Sigma a^*_{ij}(p)/N$$

$$b^*(p) = \Sigma\Sigma b^*_{ij}(p)/N \quad \text{[Expression 23]}$$

An important method for acquiring features of a sample 2 to be measured by image analysis is to obtain a distribution of measured values in the CIELAB color space. In this case again, the region from the i-th pixel to the i+I-th pixel along the X axis of the image and the region from the j-th pixel to the j+J-th pixel along the Y axis are calculated.

A method for calculating the number of colors that appeared and a method for calculating information entropy can be used as a method for representing distributions of measured values in the CIELAB color space as numerical parameters. Information entropy H can be calculated according to Formula 24.

$$H(p) = -\Sigma P(p,c) \log_2\{P(p,c)\} \quad \text{[Expression 24]}$$

Here, P(p, c) is the frequency of appearance of color c in an image taken with illumination p and is calculated by dividing the region from the i-th pixel to the i+I-th pixel along the X axis and the region from the j-th pixel to the j+J-th pixel along the Y axis into cubes with edges $\Delta L^*$, $\Delta a^*$, $\Delta b^*$ of a certain length.

Various other methods can also be used, such as a method of using an image filter or differential values, or performing frequency analysis such as Fourier transform or wavelet transform on an image position, i.e. a aspecular angle $\theta(p)$, which is a geometrical condition of illumination and light reception, and a method of parameterizing distributions in the CIELAB color space in further detail. By quantifying features of an object to be measured, the difference between two different objects to be measured can be quantified. In addition, efficiency improvement and advantageous effects in a wide range of application such as quality control in product manufacturing and determination of manufacturing methods can be achieved.

(Three-Dimensional Curved Surface)

Spectral information on a sample surface of a planar object to be measured is acquired using changes in optical geometrical conditions from pixel to pixel in the description given above. Accurate measurement of a curved surface to be measured can be made as well by incorporating a three-dimensional measurement device in a multi-angle spectral imaging apparatus and correcting optical geometrical conditions from the normal to each pixel of the curved surface.

Detailed description will be given below. Displacements in the Z axis direction of the sample surface and the normal direction are measured from the three-dimensional geometry and corrections are made to the optical geometrical conditions ($\theta_i$, $\phi_i$, $\theta_{rsv}$, $\phi_{rsv}$) described above. In the case of point light source, a position on the sample surface is denoted by $P(x_p, y_p)$, the position of a lighting device is denoted by $I(\theta_i, \phi_i, D_i)$, and the position of a light receiving device (focal position) is denoted by $R(0, 0, D_r)$. Here, x and y are positions in the X axis direction and Y axis direction, respectively, on the sample surface, $\theta$ is a zenith angle, $\phi$ is an azimuth angle measured counterclockwise from the X axis, $D_i$ is the distance from the sample surface to the light source, and $D_r$ is the distance from the sample surface to an image pickup device. It is assumed that the image pickup device has a field angle large enough to cover an image taking range of the sample surface. Geometrical conditions of illumination and light receiving at position P can be represented by the zenith angle of the illumination, the azimuth angle of the illumination, the zenith angle of the light reception, and the azimuth angle of the light reception. Then the position of the illumination can be written as:

$$x_i = D_i \cdot \sin(\theta_i) \cdot \cos(\phi_i)$$

$$y_i = D_i \cdot \sin(\theta_i) \cdot \sin(\phi_i)$$

$$z_i = D_i \cdot \cos(\theta_i) \quad \text{[Expression 25]}$$

The relative coordinate position of the illumination with respect to point P is $$x_i' = x_i - x_p$$

$$y_i' = y_i - y_p$$

$$z_i' = z_i \quad \text{[Expression 26]}$$

and the relative coordinate position of the light reception with respect to point P is $$x_r' = -x_p$$

$$y_r' = -y_p$$

$$z_r' = z_r \quad \text{[Expression 27]}$$

It is assumed here that the result of measurement of the three-dimensional geometry shows that there is a displacement of point P by $D_H$ and its normal vector is inclined at a zenith angle of $\theta_n$ in the direction of $\phi_n$. The relative coordinate position to which the displacement $D_H$ is given is $$x_i'' = x_i'$$

$$y_i'' = y_i'$$

$$z_i'' = z_i' - D_H$$

$$x_r'' = x_r'$$

$$y_r'' = y_r'$$

$$z_r'' = z_r' - D_H \quad \text{[Expression 28]}$$

If the normal vector is inclined at a zenith angle of $\theta_n$ in the $\phi_n$ direction, the same operation as rotation by $-\theta_n$ about the straight line that is perpendicular to the positions of the illumination I" and the light receiving position R" and passes through the relative coordinate X"Y" plane. The unit vector as the axis of the rotation is $(-\sin(\phi_n), \cos(\phi_n), 0)$. The general expression of the rotation $\theta$ about an arbitrary vector $(n_x, n_y, n_z)$ is

[Expression 29]
[Math 1]
Therefore, $$x_i''' = [\sin(\phi_n)^2 \cdot \{1 - \cos(-\theta_n)\} + \cos(-\theta_n)] \cdot x_i'' - \quad \text{[Expression 30]}$$
$$\sin(\phi_n) \cdot \cos(\phi_n) \cdot \{1 - \cos(-\theta_n)\} \cdot y_i'' +$$
$$\cos(\phi_n) \cdot \sin(-\theta_n) \cdot z_i''$$

$$y_i''' = -\sin(\phi_n) \cdot \cos(\phi_n) \cdot \{1 - \cos(-\theta_n)\} \cdot$$

-continued $$x_i'' + [\cos(\phi_n)^2 \cdot \{1 - \cos(-\theta)\} + \cos(-\theta_n)] \cdot y_i'' +$$
$$\sin(\phi_n) \cdot \sin(-\theta_n) \cdot z_i''$$

$$z_i''' = -\cos(\phi_n) \cdot \sin(-\theta_n) \cdot x_i'' -$$
$$\sin(\phi_n) \cdot \sin(-\theta_n) \cdot y_i'' + \cos(-\theta_n) \cdot z_i''$$

$$x_r'' = [\sin(\phi_n)^2 \cdot \{1 - \cos(-\theta_n)\} + \cos(-\theta_n)] \cdot x_r' -$$
$$\sin(\phi_n) \cdot \cos(\phi_n) \cdot \{1 - \cos(-\theta_n)\} \cdot y_r' +$$
$$\cos(\phi_n) \cdot \sin(-\theta_n) \cdot z_r'$$

$$y_r'' = -\sin(\phi_n) \cdot \cos(\phi_n) \cdot \{1 - \cos(-\theta_n)\} \cdot$$
$$x_r' + [\cos(\phi_n)^2 \cdot \{1 - \cos(-\theta_n)\} + \cos(-\theta_n)] \cdot$$
$$y_r' + \sin(\phi_n) \cdot \sin(-\theta_n) \cdot z_r'$$

$$z_r'' = -\cos(\phi_n) \cdot \sin(-\theta_n) \cdot x_r' - \sin(\phi_n) \cdot \sin(-\theta_n) \cdot y_r' +$$
$$\cos(-\theta_n) \cdot z_r'$$

Therefore the geometrical conditions ($\theta_{il}$, $\phi_{il}$, $\theta_{rsv}$, $\phi_{rsv}$) are $$\theta_{il} = \pi/2 - \tan^{-1}(z_i'''/\sqrt{(x_i''')^2 + (y_i''')^2})$$

$$\phi_{il} = \tan^{-1}(y_i'''/x_i''')$$

$$\theta_{rsv} = \pi/2 - \tan^{-1}(z_r'''/\sqrt{(x_p''')^2 + (y_p''')^2}))$$

$$\phi_{rsv} = \tan^{-1}(y_r'''/x_r''') \quad \text{[Expression 31]}$$

In the case of three-dimensional curved surface measurement, the calibration coefficients need to be corrected when there are changes in position and angle. That is, the calibration coefficient is recalculated using a displacement $D_H$ in the vertical direction and an inclination with respect to the illumination position. This is done because the irradiation energy per unit area changes with the displacement and the inclination.

Figure 37:
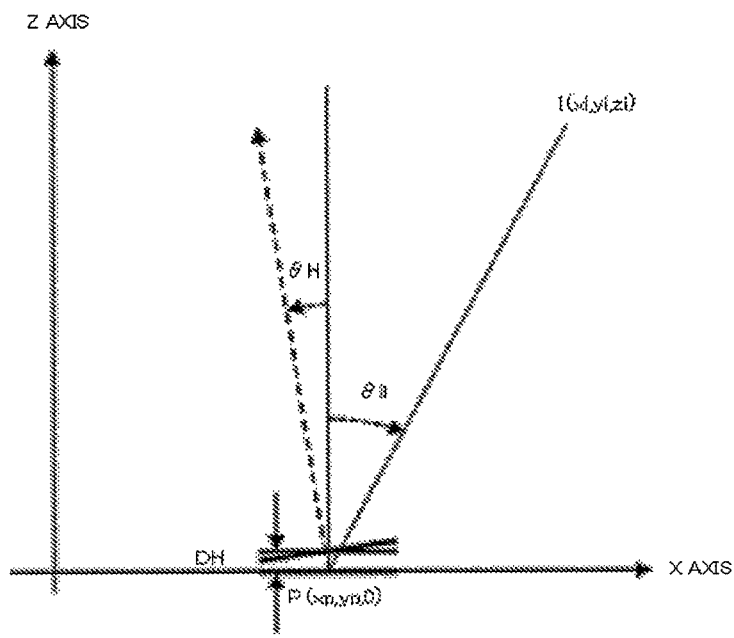
FIG. 37 is a diagram illustrating correction of a calibration coefficient.

FIG. 37 is a diagram illustrating correction of a calibration coefficient. A position on the XYZ Cartesian coordinates of the illumination is denoted by $I(x_i, y_i, z_i)$ and the observation position on the sample surface is denoted by $P(x_p, y_p, 0)$. The distance $D_I$ from the observation position to the illumination position is $$D_I = [(x_i - x_p)^2 + (y_i - y_p)^2 + z_p^2]^{0.5} \quad \text{[Expression 32]}$$

When there is a change $D_H$ in the distance, the calibration coefficient C is corrected according to the following formula.

$$C' = C \cdot (D_I + D_H)/D_I \quad \text{[Expression 33]}$$

The unit vector at point P in the direction of illumination is denoted by ($n_{Ix}$, $n_{Iy}$, $n_{Iz}$) and the unit vector of point P with respect to the three-dimensional curved surface is denoted by ($n_{Hx}$, $n_{Hy}$, $n_{Hz}$). Because the unit vector of point P in the vertical direction is (0, 0, 1), the inner product of this unit vector and the unit vector in the direction of illumination is $n_{Iz}$. Therefore the zenith angle in the direction of illumination is $$\cos(\theta_I) = n_{Iz}$$

$$\theta_I = \cos^{-1}(n_{Iz}) \quad \text{[Expression 34]}$$

In this case, the projected area of light per unit area is $$S_I = 1/\cos(\theta_I) \quad \text{[Expression 35]}$$

On the other hand, the inner product A of the direction of illumination and the normal direction is $$A = n_{Ix} \cdot n_{Hx} + n_{Iy} \cdot n_{Hy} + n_{Iz} \cdot n_{Hz}$$

$$\theta_{IH} = \cos^{-1}(A) \quad \text{[Expression 36]}$$

Therefore, the projected area in this case is $$S_{IH} = 1/\cos(\theta_{IH}) \quad \text{[Expression 37]}$$

The correction coefficient in this case is $$C'' = C \cdot (S_I/S_{IH}) = C \cdot [(D_I + D_H)/D_I] \cdot [\cos(\theta_{IH})/\cos(\theta_I)] \quad \text{[Expression 38]}$$

The method for obtaining the correction coefficient is not limited to this; any of various methods can be used.

A specific example of an embodiment of the present invention will now be described.

In this example, the monochrome two-dimensional image sensor 4 including a Peltier cooling mechanism and an anti-blooming mechanism and having 772 pixels in the X axis direction and 580 pixels in the Y axis direction was used. The imaging lens was a single-focus C mount lens having a focal length of 25 mm and a longitudinal field angle of 22 degrees. The spectroscopic means had a liquid-crystal tunable filter immediately before the lens and was capable of spectral measurement in the visible light range at intervals of 10 nm. As the sample surface to be measured, the central area of an image that has 720 pixels in the X axis direction and 520 pixels in the Y axis direction was used and the other, marginal area was a white reference surface. For illumination, two sets of linearly arranged 10 white LED chips each of which included a projection lens were provided and were disposed so that the sample surface to be measured was illuminated at angles of 20 degrees and 45 degrees from the direction perpendicular to the center of the sample surface to be measured.

In this example, before measurement, a standard white plate, which is a standard calibration plate, was set in a measurement place after power-on, then calibration information at each wavelength was measured with the illuminants at 20 degrees and 45 degrees. In order to make corrections of spectral distribution properties of the liquid-crystal tunable filter and the lighting devices, exposure time was optimized for each measurement wavelength and was stored along with the calibration information in the memory. Then, the sample to be measured was set at the measurement place and measurement was made with illuminants at 20 degrees and 45 degrees for each wavelength with the same exposure times as those in the calibration.

Figure 9:
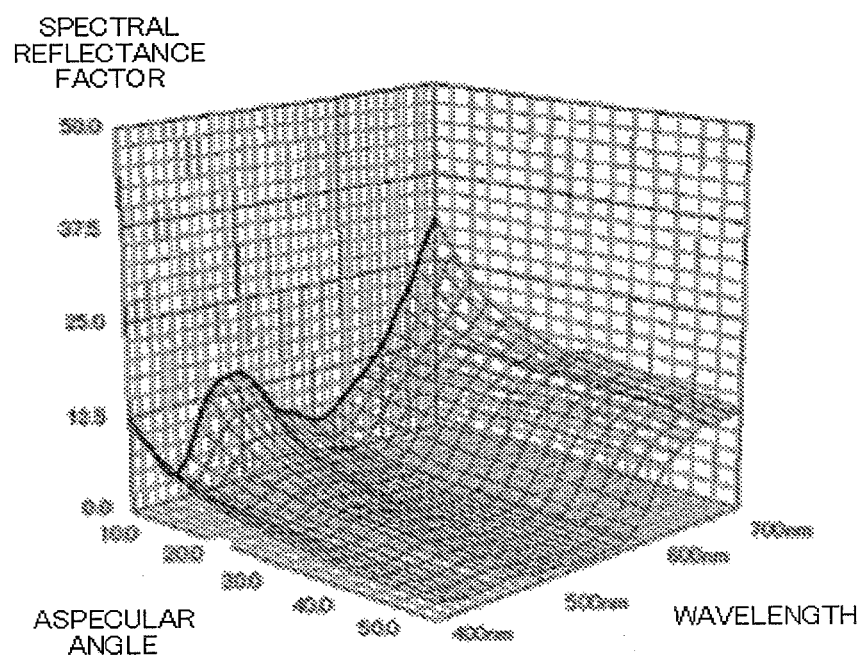
FIG. 9 is a diagram representing changes in spectral reflectance factor as wavelength and aspecular angle are changed in the present invention.

Sample A (a color card containing aluminum flake pigment (Alpate 7670 NS from Toyo Aluminium K.K.)) and sample B (a color card containing interference effect materials (Xirallic Crystal Silver XT60-10 from Merck)) were measured. After the measurement of both of the samples, spectral reflectance factors for all pixels with illuminants at 20 degrees and 45 degrees were obtained based on the calibration information. From the spectral reflection coefficients, tristimulus values XYZ, RGB values for image display, and values in the CIELAB color space were obtained. FIG. 9 illustrates a graph of results of the measurement of spectral reflectance factors obtained by dividing each of images with illuminants at 20 degrees and 45 degrees into eight regions in the X axis direction, averaging the measured values of the pixels in each of the total of 16 regions, and changing the wavelength in increments of 10 nm in the range of 400 nm to 700 nm.

In addition, distributions in the CIELAB color space for all pixels with illuminants at 20 degrees and 45 degrees, the number of colors that appeared, and information entropy were calculated from the CIELAB values.

The number of colors that appeared in the image in the CIELAB color space can be used as an indicator of a feature of the color card. In the case of a color card that uses only a pigment as coloring agent and has a paint color generally called solid color, measured values in the image are substantially the same and therefore extremely few colors appear in the image. In the case of a metallic color, the lightness and chroma particularly vary depending on the type and blending quantity of aluminum effect materials contained, pigments used in combination with the effect materials, and optical geometrical conditions, and therefore more colors appear. In the case of a pearl color, the hue as well as lightness and chroma vary according to optical geometrical conditions and, in addition, interference reflected light from fine effect materials are contained and therefore various colors appear in each individual pixel, which increases the number of appearing colors. This means that colors distribute in a wider range in the CIELAB color space. The information entropy is a numerical value indicating the amount of information in an image and can be used as an indicator of a feature of a color card, like the number of appearing colors.

L*a*b* values of each pixel were calculated using a calculation method in JIS Z8729:2004 based on Formula 7 with CIE colorimetric standard illuminant D65 specified in JIS Z8781:1999 using a color-matching function for a view angle of 10 degrees. The calculation was performed with a precision of two decimal places. Then, the CIELAB space was divided into virtual cubes with an edge of 1.00 along each of the L*, a* and b* axes, values of L*a*b* calculated for 720×520=374400 pixels in the image were assigned to the cubes, and the number of cubes containing colors of the pixels that appeared was used as the number of colors that appeared. This number of colors is denoted by N. This calculation method was also used for the image divided into eight regions.

The information entropy E was calculated according to Formula 39.

$$E = -\Sigma P(i)\log_2\{P(i)\}$$ [Expression 39]

Here, P(i) is the frequency of appearance of color i in the image and represents how many pixels are included in a cube with an edge of 1.00 along each of the L*, a* and b* axes.

Figure 10:
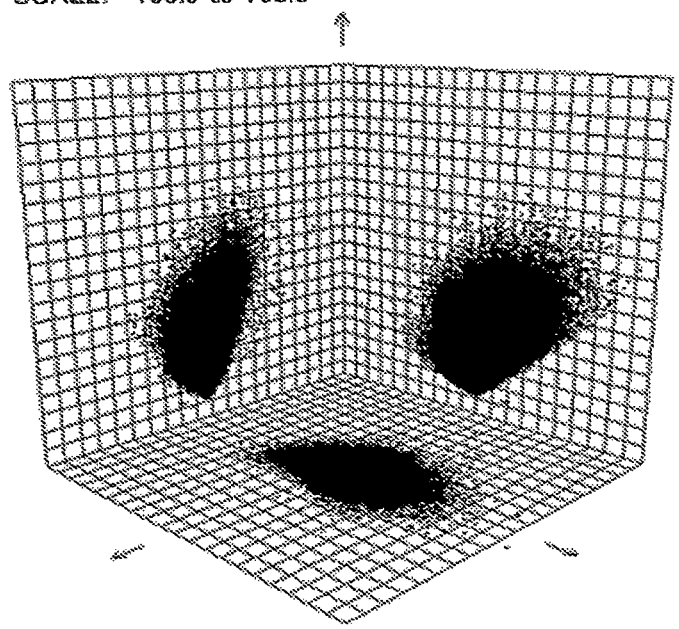
FIG. 10 is a diagram representing distributions of pixels of sample A in a CIELAB color space.
Figure 11:
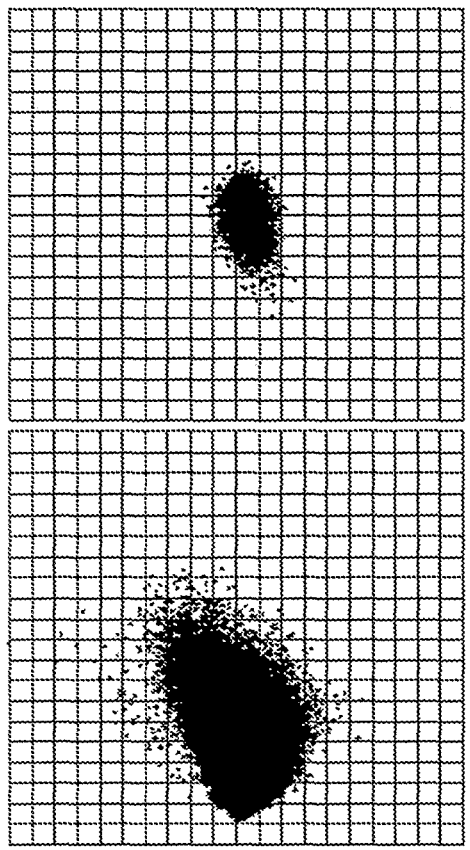
FIG. 11 is a diagram representing distributions of pixels of sample A in the CIELAB color space and representing L*-a* relationship and a*-b* relationship when a lighting device is set at angles of 20 degrees and when the lighting device is set at 45 degrees and a*-b* relationship when the value of L* is set at 50.
Figure 11:
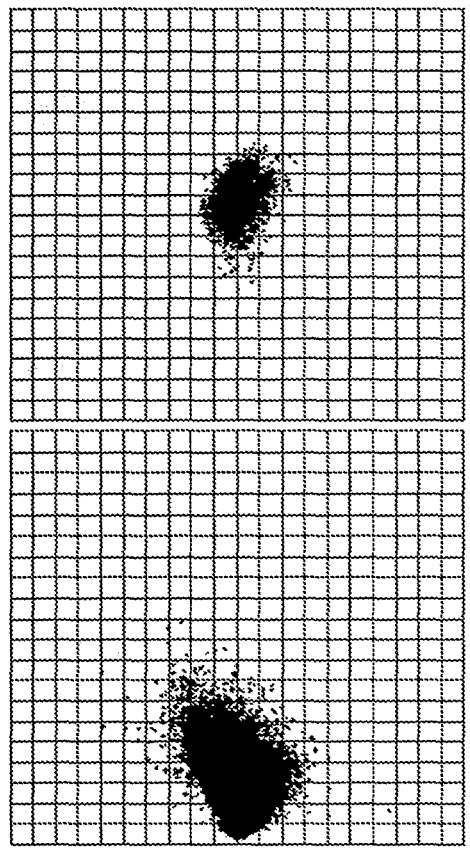
Figure 13:
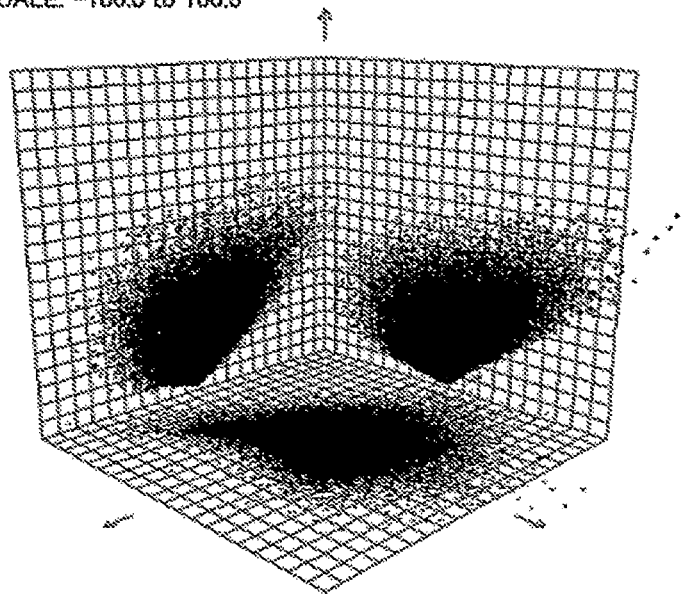
FIG. 13 is a diagram representing distributions of pixels of sample B in the CIELAB color space.
Figure 14:
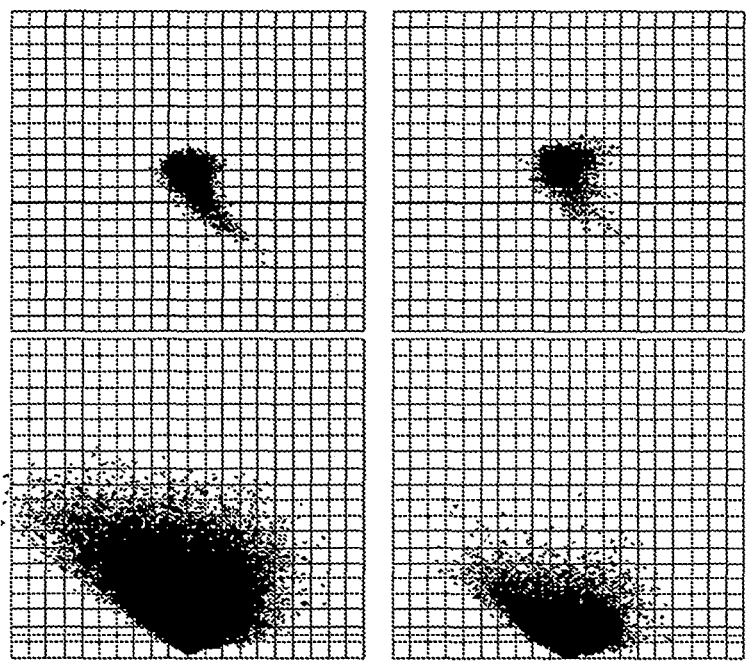
FIG. 14 is a diagram representing distributions of pixels of sample B in the CIELAB color space and representing L*-a* relationship when the lighting device is set at 20 degrees and when the lighting device is set at 45 degrees, and a*-b* relationship when the value of L* is set at 50.

FIG. 10 illustrates distributions in the CIELAB color space for sample A and FIG. 11 illustrates the L*-a* relationship with illuminants at 20 degrees and 45 degrees and the a*-b* relationship when the value of L* was set at 50. FIG. 13 illustrates distributions in the CIELAB color space for sample B and FIG. 14 illustrates the L*-a* relationship with illuminants at 20 degrees and 45 degrees and the a*-b* relationship when the value of L* was set at 50.

Figure 12:
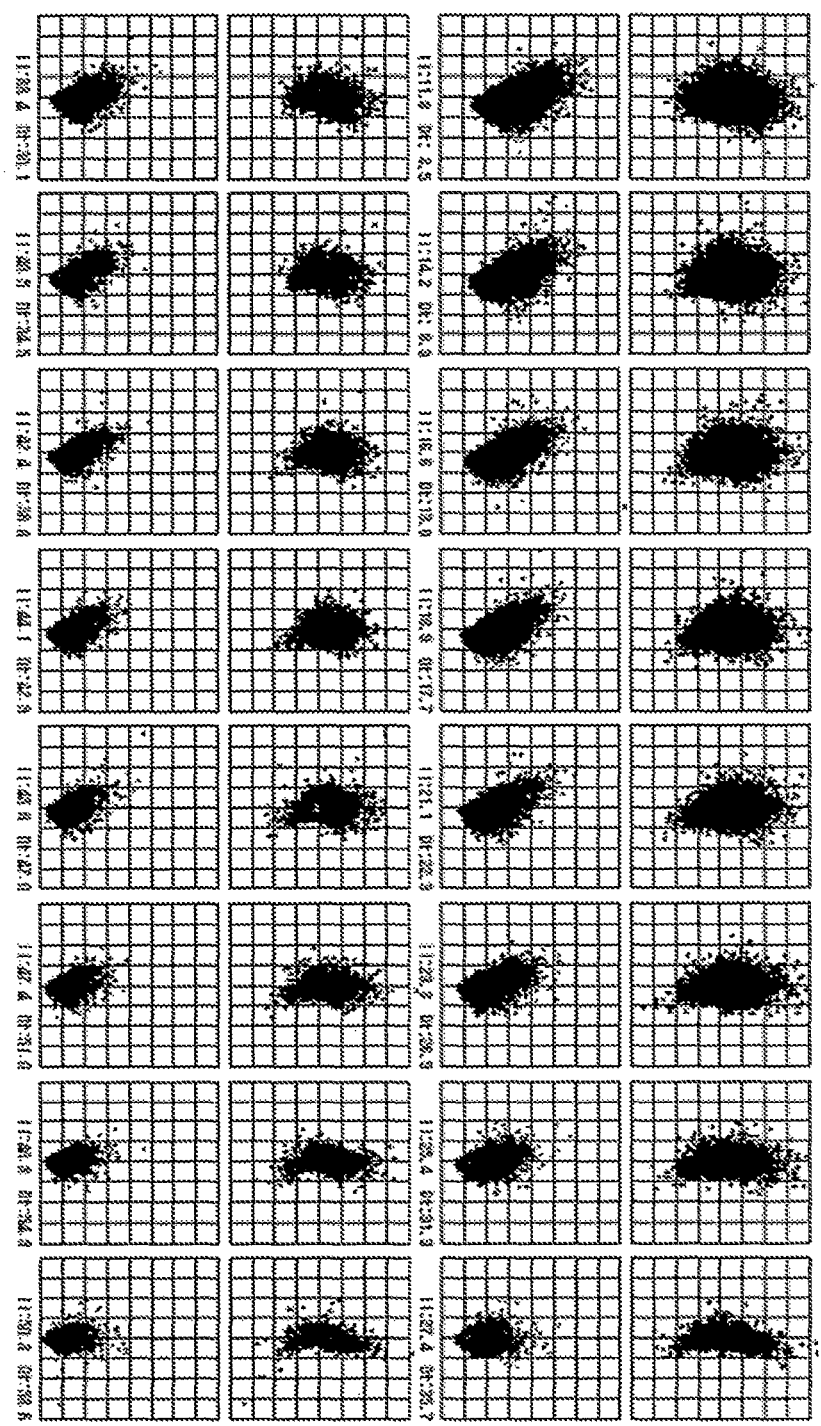
FIG. 12 is a diagram representing distributions of pixels of an image of sample A divided into eight regions with respect to a aspecular angle and representing L*-a* relationship in each region when the lighting device is set at 20 degrees and when the lighting devices is set at 45 degrees, and a*-b* relationship when the value of L* is set at 50.
Figure 15:
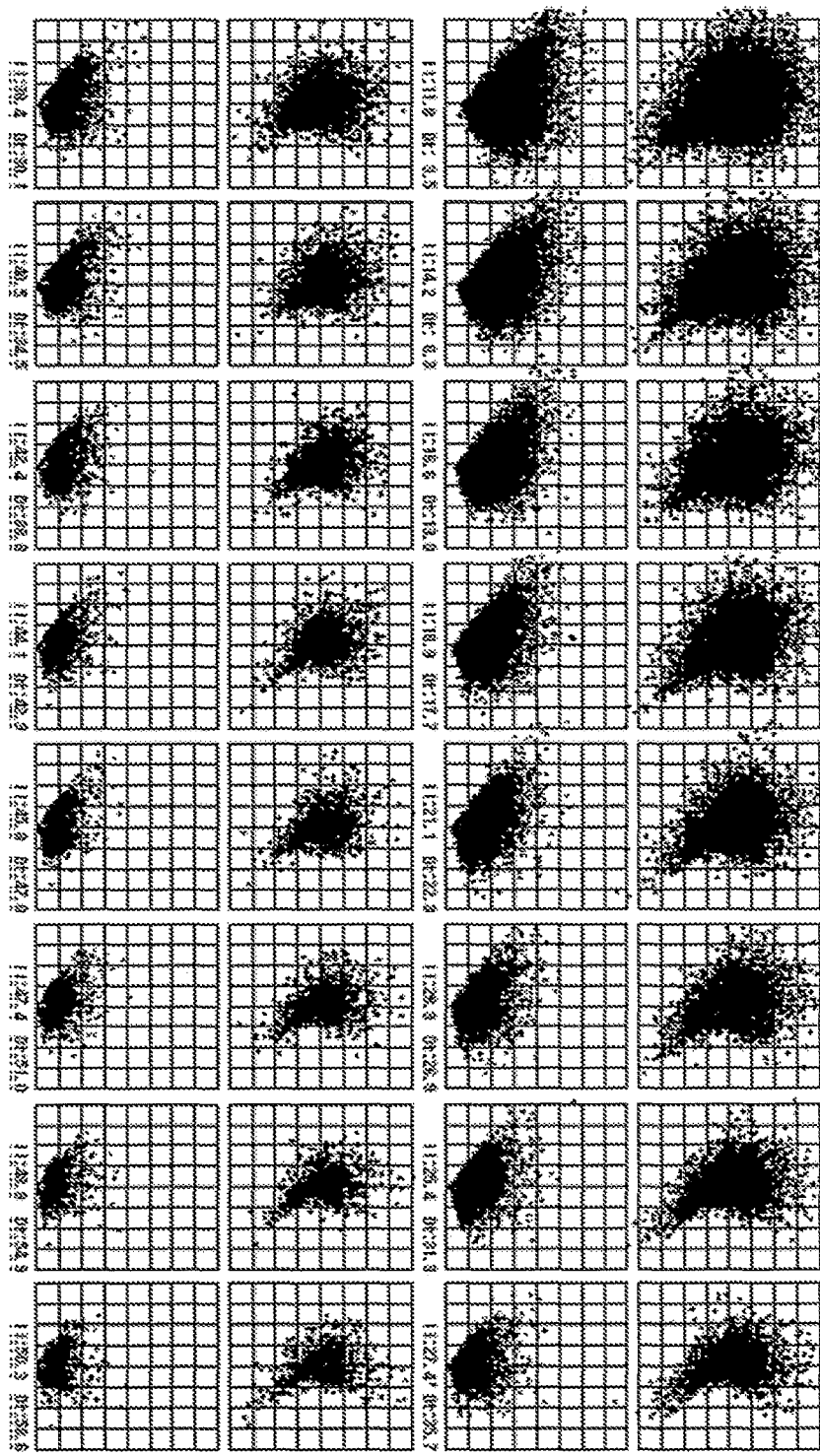
FIG. 15 is a diagram representing distributions of pixels of an image of sample B divided into eight regions with respect to a aspecular angle and representing L*-a* relationship in each region when the lighting device is set at 20 degrees and when the lighting devices is set at 45 degrees, and a*-b* relationship when the value of L* is set at 50.

Each of the images with 20-degree and 40-degree illuminants was divided into eight regions in the X axis direction. The distribution in the CIELAB color space for each region is illustrated. FIG. 12 illustrates the L*-a* relationship in the eight regions of sample A with illuminants at 20 degrees and 45 degrees and the a*-b* relationship when the value of L* was set at 50 and FIG. 15 illustrates the L*-a* relationship in the eight regions of sample B with illuminants at 20 degrees and 45 degrees and the a*-b* relationship when the value of L* was set at 50. The distributions for the interference effect materials of sample A is wider than the distributions for the aluminum effect materials of sample B because the interference effect materials of sample A have interference glittering reflections. The difference between the samples is clearly shown.

While this embodiment has been described with an example in which a white reference surface 12 is provided around a sample surface 2 to be measured, the white reference surface 12 may be omitted and only the sample surface 2 may be measured. While a white light source is used as the lighting device 10 in this embodiment, a light source that has dispersion facility in the lighting device and is capable of emitting single-wavelength light may be used.

A flat object to be measured is used to acquire spectral information of a sample surface from changes in optical geometrical conditions of each pixel in this embodiment. If surface to be measured is curved, a three-dimensional geometry measurement device may be incorporated in the multi-angle spectral imaging apparatus so that optical geometrical conditions can be accurately corrected based on the normal to each of the pixels on the curved surface.

Figure 16:
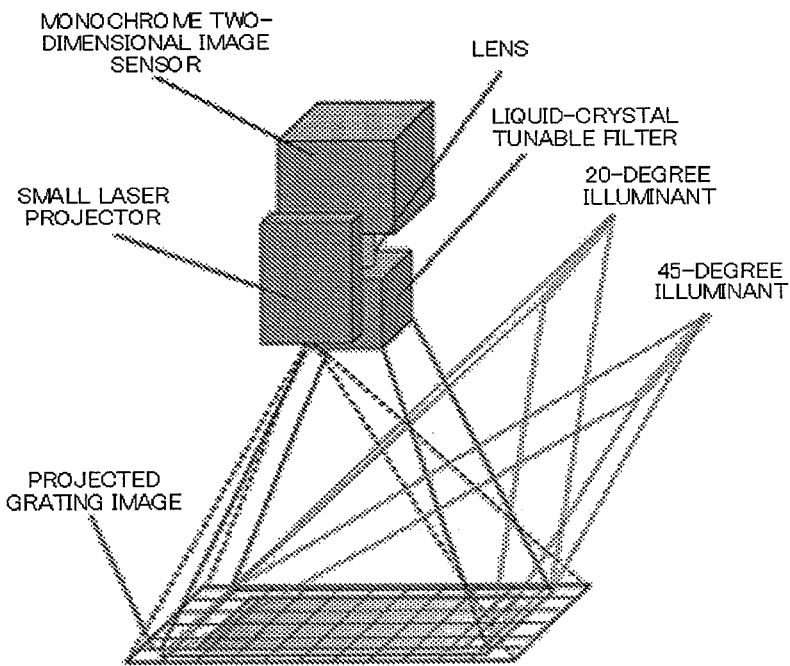
FIG. 16 is a diagram illustrating another example of the present invention that incorporates three-dimensional geometry measurement means.

Another example in which a three-dimensional geometry measurement device is incorporated will be described with reference to FIG. 16. Description of the same components as those in the example described above will be omitted.

This example includes, as in the first example, a monochrome two-dimensional image sensor 4, a liquid-crystal tunable filter which acts as spectroscopic means 6, and a lighting device 10 including two sets of linearly arranged 10 white LED chips. In addition to these components, this example includes a laser projector 9 (SHOWWX from Microvision, Inc., USA) as geometry measurement means for three-dimensional geometry correction of a sample to be measured. The laser projector 9 is used to project a grating image 11 onto a surface to be measured, the grating image 11 is captured with the monochrome two-dimensional image sensor 4, and a geometry is obtained from displacements of the grating image 11.

In this example, before measurement, a sufficiently flat standard white plate, which is a standard calibration plate, was set in a measurement place after power-on and then calibration information at each wavelength was measured with illuminants at 20 degrees and 45 degrees. Then, the laser projector 9 for three-dimensional geometry measurement was used to project a grating image, an image of the projected grating image was taken with the monochrome two-dimensional image sensor 4, and positions on the grating image 11 were quantified as data on a reference flat surface and stored.

During measurement, the grating image 11 was projected with the laser projector 9, the grating image was acquired with the monochrome two-dimensional image sensor 4, and position information on the grating image 11 on the reference flat surface that has measured and stored beforehand was used to calculate three-dimensional geometry data by a triangular method.

Then a normal vector at each of the positions on the sample surface was calculated from the calculated three-dimensional geometry data, the specular reflection direction of illumination from the lighting device was corrected, then aspecular angles were recalculated to correct optical geometrical conditions of the three-dimensional surface.

In this embodiment, optical geometrical conditions can be accurately corrected because the three-dimensional geometry measurement device is incorporated in the multi-angle spectral imaging apparatus in order to measure a curved surface to be measured. In particular, when data on aspecular angles is obtained, normal vectors are calculated from the three-dimensional geometry, specular reflection directions of illumination are corrected, then the aspecular angles are recalculated, thereby enabling measurement unaffected by the geometry of the surface to be measured.

While a surface of a solid is measured in this embodiment, an object other than solids, such as a fluid surface, liquid, and powder, can be measured contactlessly.

REFERENCE NUMERALS

2 Sample surface (sample surface to be measured)
3 White calibration plate
4 Two-dimensional image sensor
6 Spectroscopic means
8 Optical lens
9 Laser projector
10 Lighting device
11 Grating image
12 White reference surface
14 Aspecular angle
16 Unit vector in specular reflection direction
18 Unit vector in light receiving direction
19 Pixel (i, j)
20 Unit vector in illumination direction
32 Lighting direction
34 Specular reflection direction
36 Observation direction
38 Normal direction of effect materials
40 Spectral light source device
50 Housing
52 Measurement window
54 Large sample such as fender or door
56 Liquid sample

What is claimed is:

1. A multi-angle spectral imaging measurement apparatus comprising:
   a linear or point light source capable of emitting white illumination light perpendicularly onto a sample surface containing effect materials from two or more fixed angular directions;
   spectroscopic means for dispersing light reflected from the sample surface, the spectroscopic means being disposed above the sample surface;
   an imaging lens forming an image of reflected light dispersed by the spectroscopic means;
   a fixed two-dimensional image sensor capable of receiving the reflected light through the imaging lens to take an image of the sample surface; and
   a white reference surface provided around the entire sample surface;
   the multi-angle spectral imaging measurement apparatus acquiring spectral information on the sample surface by using changes in optical geometrical conditions in an illumination direction and an image taking direction for each pixel in a two-dimensional image taken with the two-dimensional image sensor;
   wherein, during calibration before measurement, an image of a reference standard white plate and the white reference surface is taken at the same time, a calibration coefficient for each pixel and each wavelength is measured, and exposure time for each of the wavelengths is determined;
   a two-dimensional image of the sample surface and the white reference surface provided around the entire sample surface is taken at each measurement wavelength by a changing a pass wavelength of the spectroscopic means without changing the relative positions of the lighting device, the two-dimensional image sensor, the sample surface and the white reference surface, and spectral information on all of the pixels of the two-dimensional image at each measurement wavelength is acquired; and
   image taking exposure time for calibration and measurement is changed according to each of the measurement wavelengths to correct gain differences in a spectral property of the lighting device, a spectral property in the spectroscopic means, and a spectral property of the two-dimensional image sensor within the range of the measurement wavelengths.

2. The multi-angle spectral imaging measurement apparatus according to claim 1,
   wherein a dynamic range of measurement is extended by changing the light amount of the lighting device or changing exposure time during image taking, or combination of both.

3. The multi-angle spectral imaging measurement apparatus according to claim 1,
   wherein the spectral information on each pixel for each measurement wavelength is used for averaging of numerical values and image calculations such as calculations of distributions of color numerical values in a color space, spatial frequency analysis image calculations, and information entropy image calculations.

4. The multi-angle spectral imaging measurement apparatus according to claim 1 into which three-dimensional geometry measurement means is incorporated,
   wherein three-dimensional geometry information on the sample surface is measured by the three-dimensional geometry measurement means, the three-dimensional geometry information on the sample surface is used to obtain the direction normal to each position on the sample surface, and changes in the optical geometrical conditions are corrected.

5. A multi-angle imaging measurement method for acquiring spectral information on all pixels in a two-dimensional image at each measurement wavelength,
   wherein an image of a reference standard white plate and a white reference surface is taken at the same time by using a linear or point light source, a calibration coefficient for each pixel and each wavelength is measured, and exposure time for each wavelength is determined during calibration before measurement, then a sample surface and a white reference surface provided around the entire sample surface are illuminated with illumination light perpendicularly to the sample surface and the white reference surface from two or more fixed angular directions, illumination light reflected from the sample surface and the white reference surface is dispersed by spectroscopic means, the dispersed reflected light is imaged by an imaging lens, the reflected light is received through the imaging lens, an image of the received light is taken by a fixed two-dimensional image sensor without changing the relative positions of the lighting device, the two-dimensional image sensor, the sample surface and the white reference surface, changes in the amount of illumination light and changes in exposure time during measurement are corrected with reference to light reflected at the white reference surface, changes in optical geometrical conditions in an illumination direction and an image taking direction of each pixel in the two-dimensional image taken are used to acquire spectral information on the sample surface; and
   image taking exposure time during calibration and measurement are changed according to each measurement wavelength to correct gain differences in a spectral property of the lighting device, a spectral property in the spectroscopic means, and a spectral property of the two-dimensional image sensor within the range of the measurement wavelengths.

6. The multi-angle imaging measurement method according to claim 5, wherein three-dimensional geometry information on the sample surface is measured by three-dimensional geometry measurement means, the three-dimensional geometry information on the sample surface is used to obtain the direction normal to each position on the sample surface, changes in the optical geometrical conditions are corrected.

7. A method for calculating a spectral reflectance factor for each measurement wavelength associated with multi-angle information, image distributions in spatial frequency analysis and fractal analysis, distributions in a color space that are obtained from a color value of each pixel, the number of appearing colors, and information entropy by using a spectral reflectance factor of each pixel or a numerical color value in a color space calculated from the spectral reflectance factor on the basis of spectral information on each pixel obtained by the multi-angle spectral imaging measurement apparatus according to claim 1.

* * * * *